(12) United States Patent
Sekiguchi et al.

(10) Patent No.: US 9,786,806 B2
(45) Date of Patent: Oct. 10, 2017

(54) SEMICONDUCTOR DEVICE AND METHOD FOR MANUFACTURING THE SAME

(71) Applicant: CANON KABUSHIKI KAISHA, Tokyo (JP)

(72) Inventors: Ryota Sekiguchi, Tokyo (JP); Toshihiko Ouchi, Machida (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/106,996

(22) PCT Filed: Dec. 22, 2014

(86) PCT No.: PCT/JP2014/006359
§ 371 (c)(1),
(2) Date: Jun. 21, 2016

(87) PCT Pub. No.: WO2015/098073
PCT Pub. Date: Jul. 2, 2015

(65) Prior Publication Data
US 2016/0351744 A1    Dec. 1, 2016

(30) Foreign Application Priority Data

Dec. 25, 2013   (JP) .................................. 2013-267156
Dec. 3, 2014    (JP) .................................. 2014-245236

(51) Int. Cl.
*G01N 21/3581* (2014.01)
*H01L 31/112* (2006.01)
(Continued)

(52) U.S. Cl.
CPC ............ *H01L 31/1123* (2013.01); *G01J 1/44* (2013.01); *H01L 27/0629* (2013.01);
(Continued)

(58) Field of Classification Search
CPC ................... H01L 25/50; H01L 27/092; H01L 2924/12032; H01L 27/1463;
(Continued)

(56) References Cited

U.S. PATENT DOCUMENTS 5,926,705 A      7/1999  Nishida
2005/0167709 A1* 8/2005  Augusto ........... H01L 27/14643
                                                           257/292
(Continued)

FOREIGN PATENT DOCUMENTS

JP   09-008271 A    1/1997
JP   3312058 B2     8/2002
(Continued)

OTHER PUBLICATIONS

Han et al., "Terahertz Image Sensors Using CMOS Schottky Barrier Diodes", ISOCC Nov. 4, 2012, SOC Design Conference, pp. 254-257.

(Continued)

*Primary Examiner* — David Porta
*Assistant Examiner* — Faye Boosalis
(74) *Attorney, Agent, or Firm* — Canon U.S.A., Inc. IP Division

(57) ABSTRACT

A semiconductor device includes a silicon substrate and a detection element and p-type and n-type MOS transistors, which are arranged on the silicon substrate, wherein the detection element includes a semiconductor layer, electrodes, and a Schottkey barrier disposed therebetween, the semiconductor layer is arranged just above a layer having the same composition and height as those of an impurity diffusion layer in the source or drain of the p-type or n-type MOS transistor, a region, in the silicon substrate, having the same composition and height as those of a channel region, in the silicon substrate, just below a gate oxide film of the (Continued)

p-type MOS transistor or the n-type MOS transistor, or a region, in the silicon substrate, having the same composition and height as those of a region just below a field oxide film disposed between the p-type and the n-type MOS transistor.

16 Claims, 10 Drawing Sheets

(51) Int. Cl.
*H01L 29/872* (2006.01)
*H01L 27/06* (2006.01)
*H01L 31/108* (2006.01)
*H01L 31/18* (2006.01)
*H01L 29/66* (2006.01)
*G01J 1/44* (2006.01)
*H01L 27/146* (2006.01)

(52) U.S. Cl.
CPC .... *H01L 27/1463* (2013.01); *H01L 27/14649* (2013.01); *H01L 27/14689* (2013.01); *H01L 29/66143* (2013.01); *H01L 29/872* (2013.01); *H01L 31/1085* (2013.01); *H01L 31/1804* (2013.01); *G01J 2001/4446* (2013.01); *G01N 21/3581* (2013.01); *Y02E 10/547* (2013.01); *Y02P 70/521* (2015.11)

(58) Field of Classification Search
CPC ............. H01L 27/0629; H01L 31/1804; H01L 31/1085; H01L 31/1123; G01J 2001/4446; G01N 21/3581
See application file for complete search history.

(56) References Cited

U.S. PATENT DOCUMENTS

| 2007/0210351 | A1* | 9/2007 | Tsuchiya | ......... H01L 21/823835 |
| | | | | 257/288 |
| 2009/0057770 | A1 | 3/2009 | Pang | |

FOREIGN PATENT DOCUMENTS

| JP | 2008-306080 A | 12/2008 |
| JP | 2010-062533 A | 3/2010 |
| JP | 2013-038390 A | 2/2013 |
| WO | 2013/008687 A1 | 1/2013 |

OTHER PUBLICATIONS

Han et al.,"A 280-GHz Schottky Diode Detector in 130-nm Digital CMOS", IEEE Journal of Solid-State Circuits, vol. 46, No. 11, Nov. 2011.

Walter H Kohl, "Materials and Techniques for Electron Tubes", The publisher: Reinhold Pub. Corp, Jan. 1960, pp. 526.

* cited by examiner

[Fig. 1]
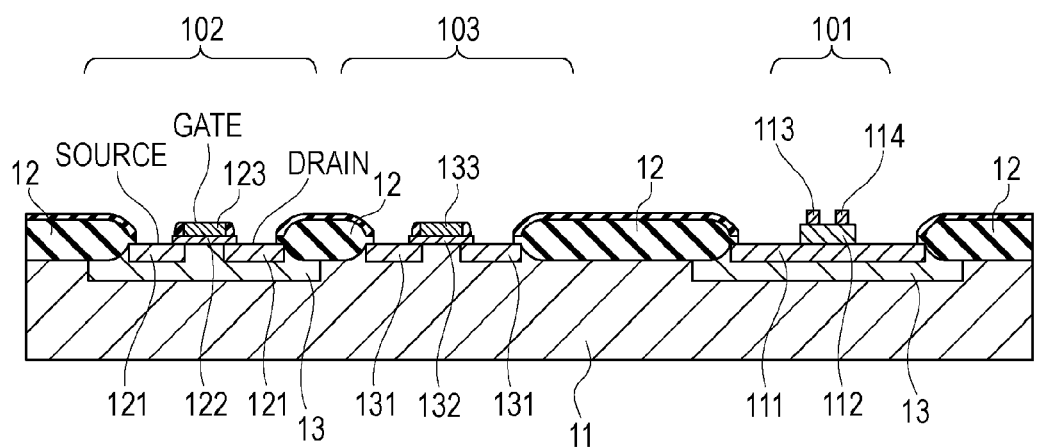
[Fig. 2]
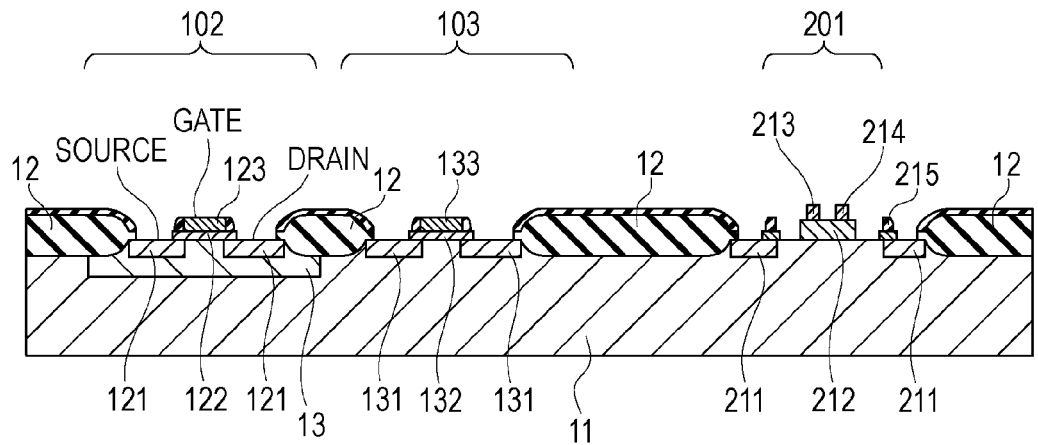

[Fig. 3]
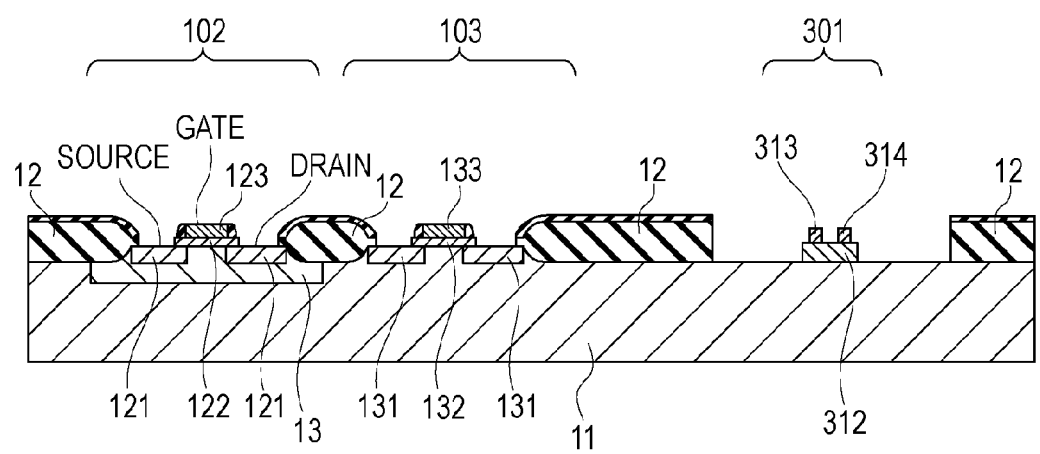
[Fig. 4]
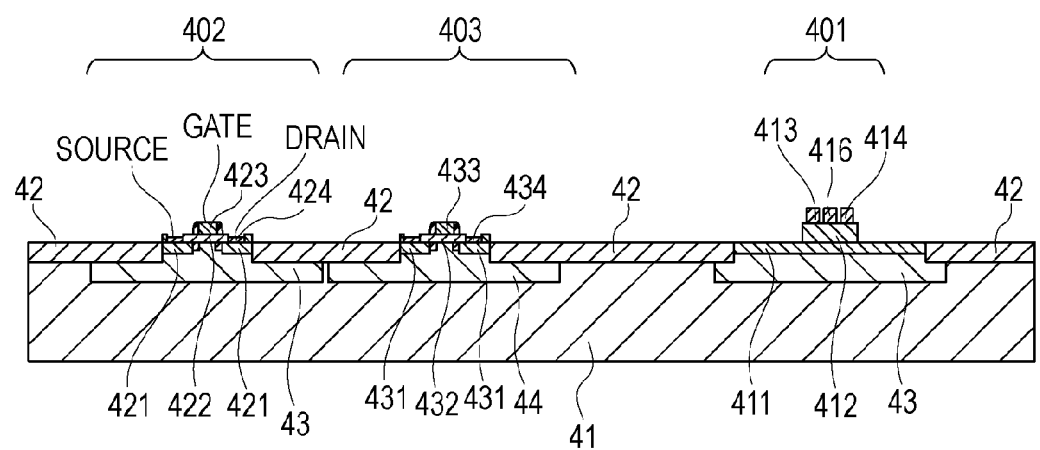

[Fig. 5]
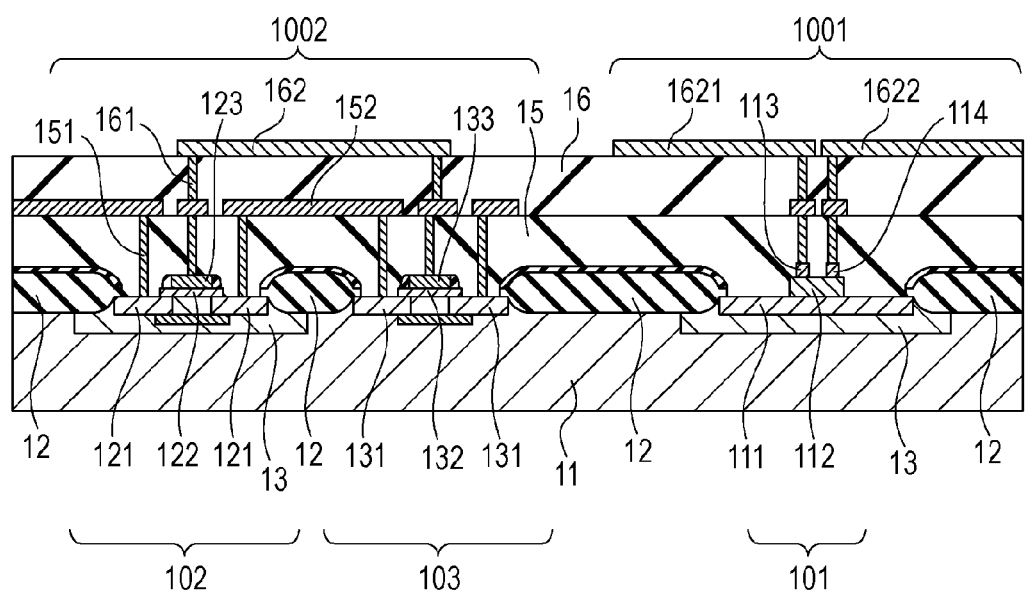
[Fig. 6A]
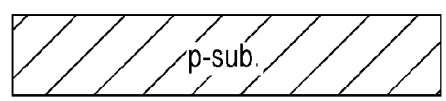

[Fig. 6B]
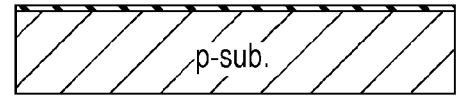
[Fig. 6C]
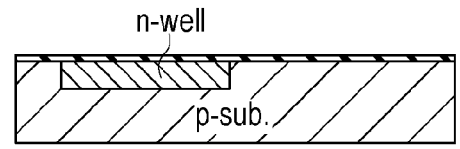
[Fig. 6D]
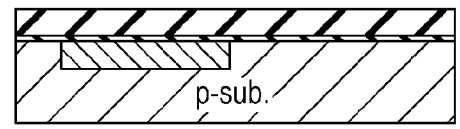
[Fig. 6E]
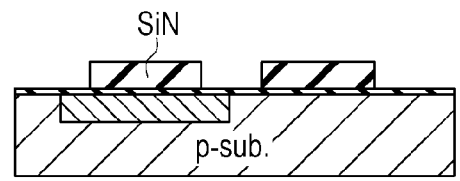
[Fig. 6F]
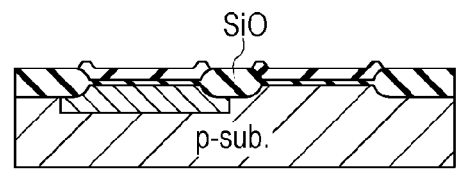
[Fig. 6G]
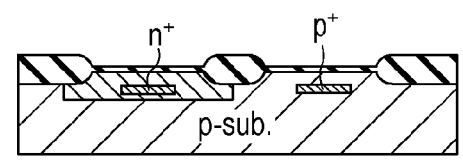
[Fig. 6H]
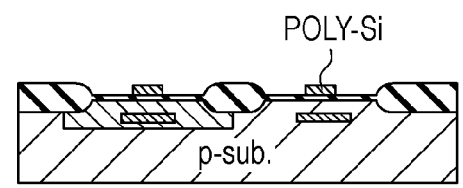

[Fig. 6I]
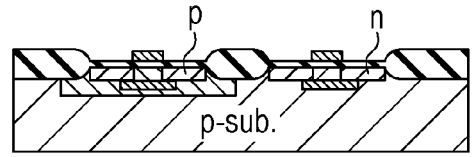
[Fig. 6J]
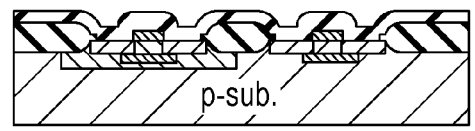
[Fig. 6K]
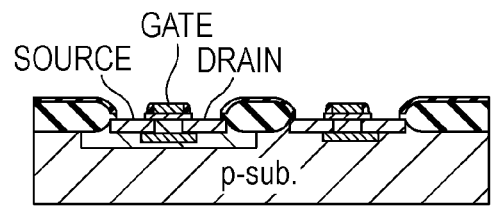
[Fig. 7A]
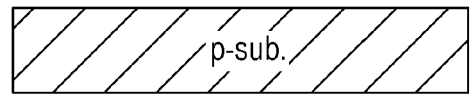
[Fig. 7B]
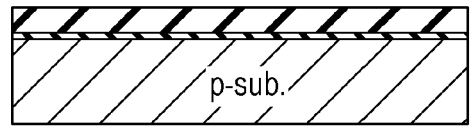
[Fig. 7C]
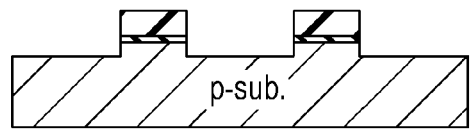
[Fig. 7D]
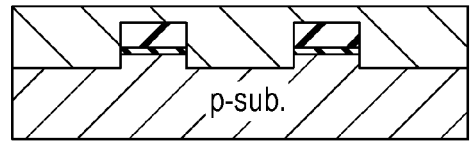

[Fig. 7E]
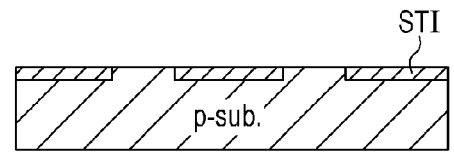
[Fig. 7F]
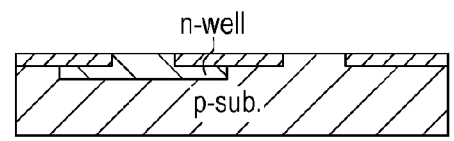
[Fig. 7G]
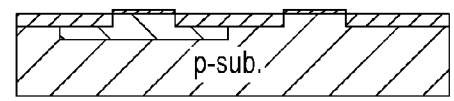
[Fig. 7H]
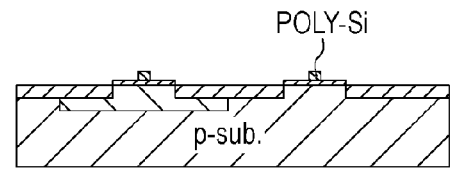
[Fig. 7I]
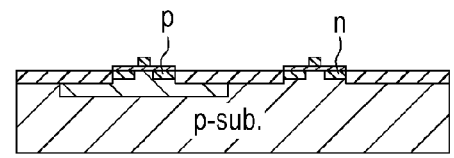
[Fig. 7J]
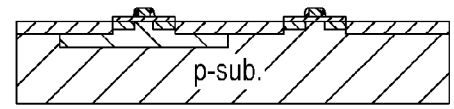
[Fig. 7K]
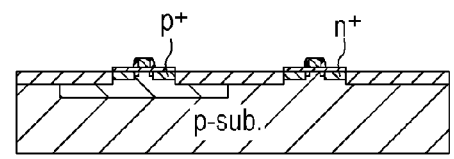
[Fig. 7L]
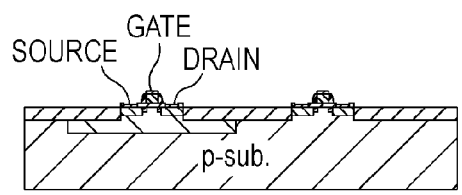

[Fig. 8A]
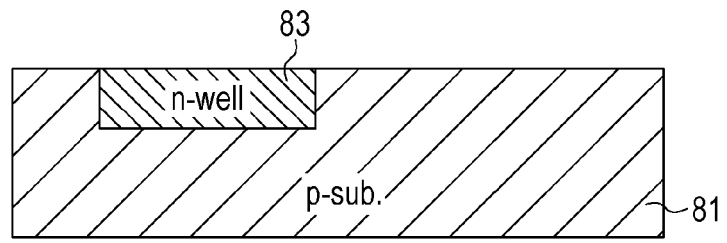
[Fig. 8B]
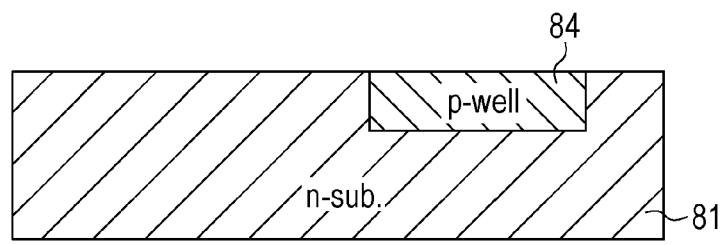
[Fig. 8C]
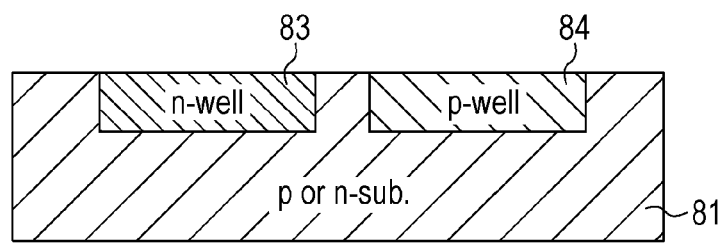
[Fig. 8D]
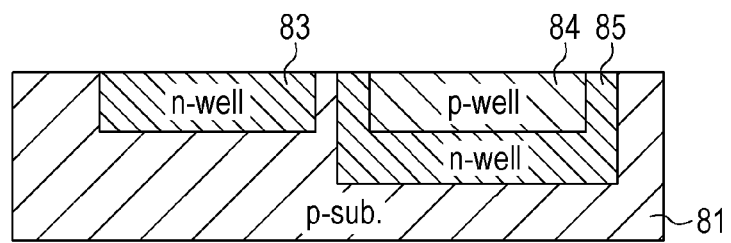

[Fig. 9A]
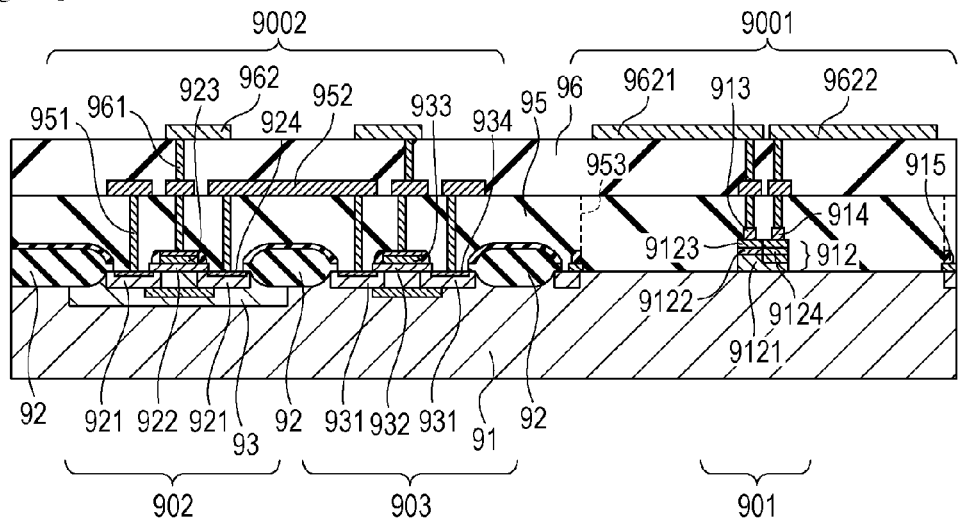
[Fig. 9B]
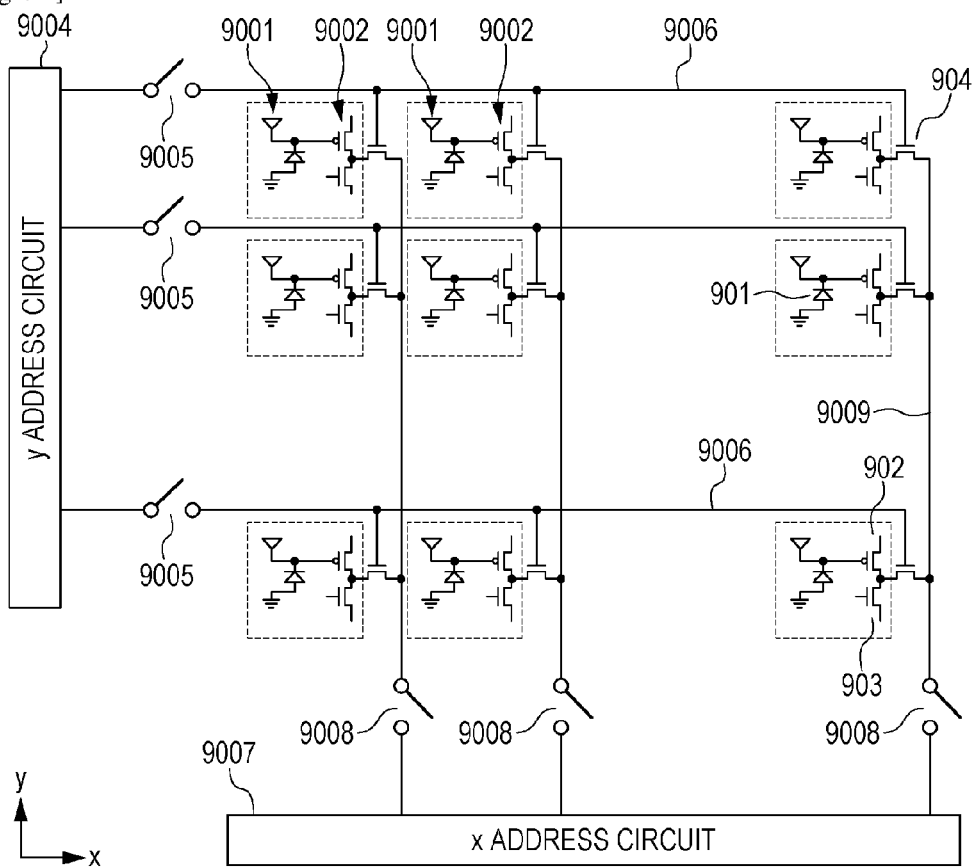

[Fig. 10A]
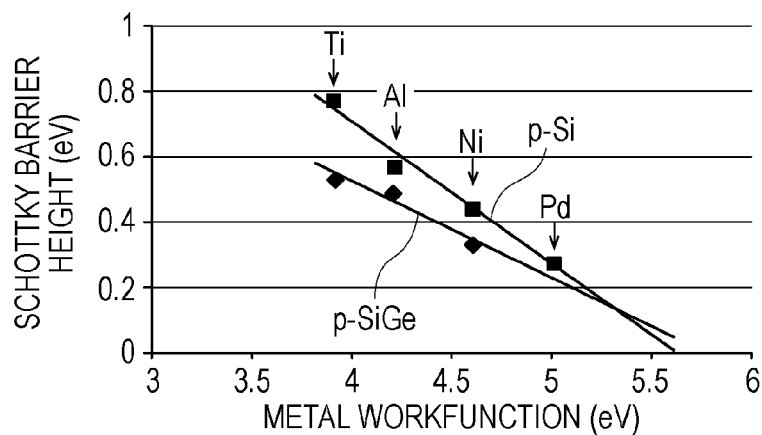
[Fig. 10B]
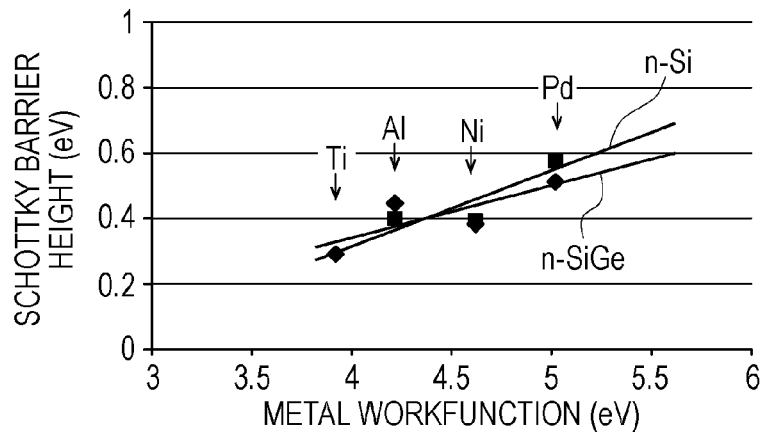
[Fig. 10C]
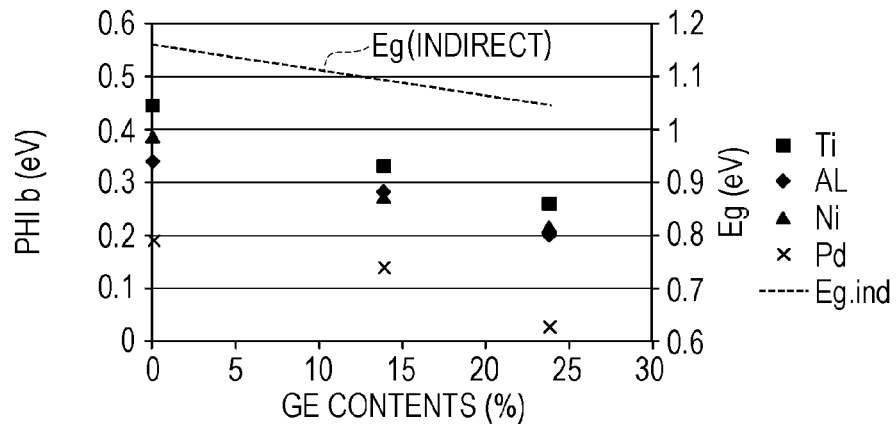

[Fig. 11A]
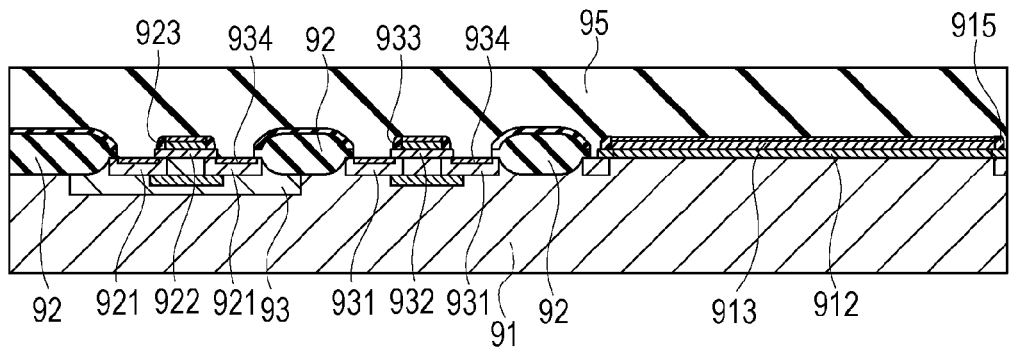
[Fig. 11B]
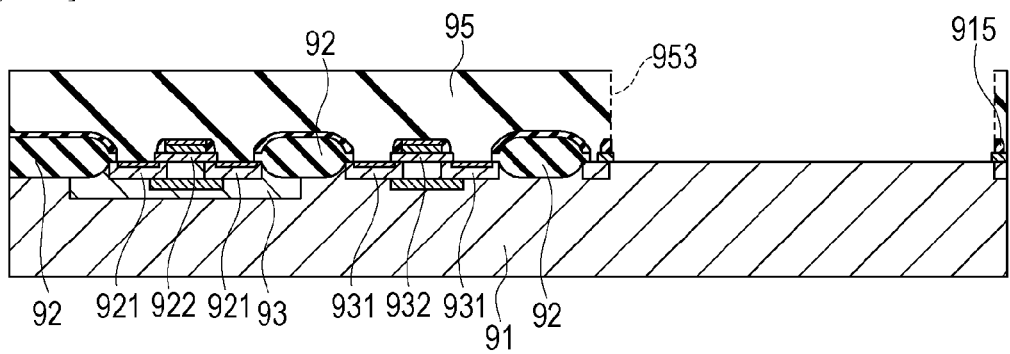
[Fig. 11C]
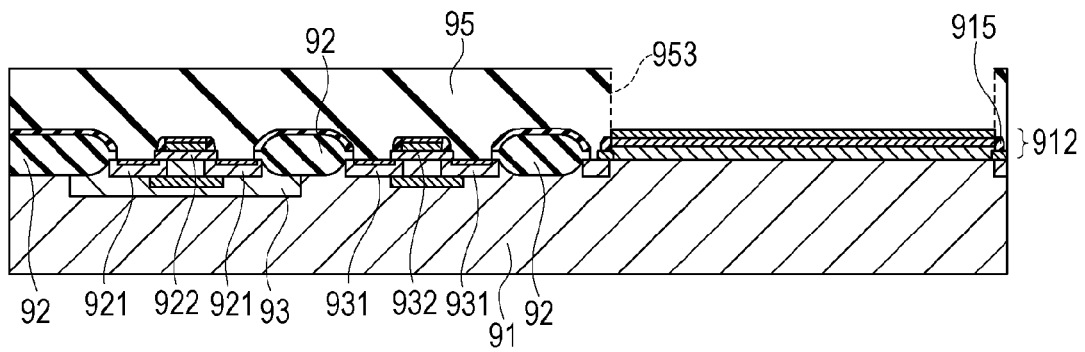
[Fig. 11D]
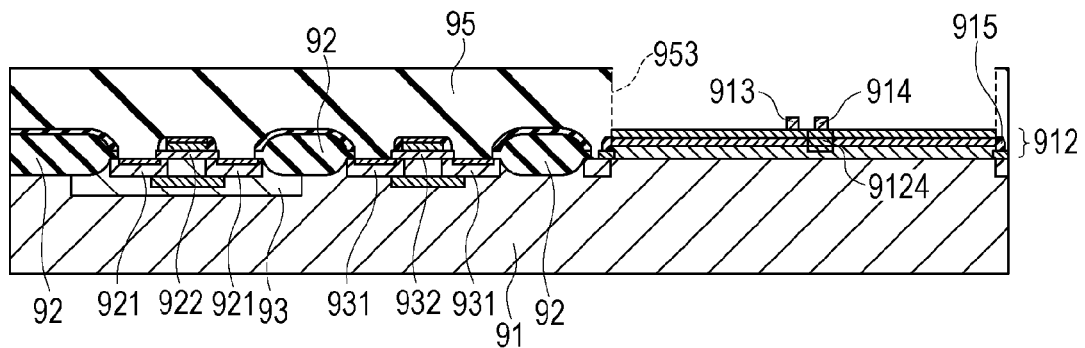

SEMICONDUCTOR DEVICE AND METHOD FOR MANUFACTURING THE SAME

TECHNICAL FIELD

The present invention relates to a semiconductor device and a method for manufacturing the same.

BACKGROUND ART

In recent years, image forming apparatuses, which detect electromagnetic waves in frequency bands lower than the visible light region and the near-infrared region and image the intensity thereof on a two-dimensionally arranged pixel basis, have been developed. In such image forming apparatuses, imaging elements in which detection elements are integrated in a two-dimensional array are favorably used for performing imaging in one shot. This is because an imaging time is reduced considerably as compared with the imaging time in the method in which the individual detection elements are scanned. In that case, it is necessary that, typically, the detection elements be integrated together with control elements and the like on the same substrate.

PTL 1 discloses a technology to integrate Schottkey barrier diodes for millimeter waves on the same substrate as the substrate of heterostructure field-effect transistors. In this semiconductor device, a Schottkey barrier diode layer and a heterostructure field-effect transistor layer are stacked by epitaxial growth on a substrate in that order and an isolation layer serving as both an etching stopper layer and an insulating layer is provided between the layers. The Schottkey barrier diode is allowed to function as an element for detecting electromagnetic waves and, therefore, may be used for not only communications described in PTL 1 but also a millimeter wave imaging device by employing such a technology.

The configuration in which silicon (Si) is used as a relatively inexpensive semiconductor device has been studied. The mobility of Si is low as compared with the mobility of the III-V compound semiconductor because the microfabrication technology has been developed. Submicron scale microfabrication allows reduction of various time constants of structure causing delay in electromagnetic waves. In addition, Si has an advantage that it is possible to use a complementary metal oxide semiconductor (Complementary MOS, CMOS) as a control element.

NPL 1 discloses a technology to integrate the Schottkey barrier diode and the CMOS on the same substrate by using a standard CMOS process. In a disclosed method, the Schottkey barrier diode is formed by using the CMOS process, wherein in the CMOS process under 130 nm design rule, a technique to make a contact hole on an n-well structure and fill a metal into the contact hole is employed. The Schottkey barrier diode is integrated on a Si substrate together with a 280-GHz receiving antenna and a first-stage low noise amplifier (LNA) and serves as a high-sensitivity, low-noise detection element.

It is believed that such a configuration on the Si substrate is relatively inexpensive because production is performed by the standard CMOS process which has been completed as a process and, in addition, is suitable for an increase in the number of pixels in consideration of the diameters of wafers which have been already distributed.

CITATION LIST

Patent Literature

PTL 1: Japanese Patent No. 3312058

Non Patent Literature

NPL 1: R. Han et al, IEEE Journal of Solid-state Circuits, vol. 46, No. 11, 2602 (2011)

SUMMARY OF INVENTION

However, the semiconductor device in PTL 1 has a structure for the individual elements and the applicability to an imaging element having the large number of pixels, e.g., 100 pixels per line, is poor. Meanwhile, in NPL 1, there are design limitations to the structure of the Schottkey barrier diode which can be formed by the CMOS process. Specifically, for example, change of the semiconductor material in a metal-semiconductor contact portion important for the Schottkey barrier diode is difficult, it is not possible to subject the semiconductor surface to a treatment, and the size and the material of the metal are not selectable. Consequently, it is difficult to adjust the rectification characteristics and electromagnetic wave detection characteristics to predetermined states, and a relatively large bias voltage may be required.

A semiconductor device according to an aspect of the present invention is a semiconductor device including a silicon substrate and a detection element, a p-type MOS transistor, and an n-type MOS transistor which are arranged in an in-plane direction on the silicon substrate, wherein the detection element includes a semiconductor layer and electrodes, where a Schottkey barrier is disposed between the semiconductor layer and the electrodes, the semiconductor layer is arranged (i) just above a layer having the same composition and height as those of an impurity diffusion layer in the source or drain of the p-type MOS transistor, (ii) just above a layer having the same composition and height as those of an impurity diffusion layer in the source or drain of the n-type MOS transistor, (iii) just above a region, in the silicon substrate, having the same composition and height as those of a channel region, in the silicon substrate, just below a gate oxide film of the p-type MOS transistor or the n-type MOS transistor, or (iv) just above a region, in the silicon substrate, having the same composition and height as those of a region, in the silicon substrate, just below a field oxide film disposed between the p-type MOS transistor and the n-type MOS transistor.

Further aspects of the present invention will become apparent from the following description of exemplary embodiments with reference to the attached drawings.

BRIEF DESCRIPTION OF DRAWINGS

FIG. 1 is a sectional view showing part of a semiconductor device according to a first embodiment.

FIG. 2 is a sectional view showing part of a semiconductor device according to a second embodiment.

FIG. 3 is a sectional view showing part of a semiconductor device according to a third embodiment.

FIG. 4 is a sectional view showing part of a semiconductor device according to a fourth embodiment.

FIG. 5 is a sectional view showing part of a semiconductor device according to a fifth embodiment.

FIG. 6A is a sectional view illustrating a front end process in a LOCOS method as a standard CMOS process.

FIG. 6B is a sectional view illustrating the front end process in the LOCOS method as the standard CMOS process.

FIG. 6C is a sectional view illustrating the front end process in the LOCOS method as the standard CMOS process.

FIG. 6D is a sectional view illustrating the front end process in the LOCOS method as the standard CMOS process.

FIG. 6E is a sectional view illustrating the front end process in the LOCOS method as the standard CMOS process.

FIG. 6F is a sectional view illustrating the front end process in the LOCOS method as the standard CMOS process.

FIG. 6G is a sectional view illustrating the front end process in the LOCOS method as the standard CMOS process.

FIG. 6H is a sectional view illustrating the front end process in the LOCOS method as the standard CMOS process.

FIG. 6I is a sectional view illustrating the front end process in the LOCOS method as the standard CMOS process.

FIG. 6J is a sectional view illustrating the front end process in the LOCOS method as the standard CMOS process.

FIG. 6K is a sectional view illustrating the front end process in the LOCOS method as the standard CMOS process.

FIG. 7A is a sectional view illustrating a front end process in a trench-type isolation method as a standard CMOS process.

FIG. 7B is a sectional view illustrating the front end process in the trench-type isolation method as the standard CMOS process.

FIG. 7C is a sectional view illustrating the front end process in the trench-type isolation method as the standard CMOS process.

FIG. 7D is a sectional view illustrating the front end process in the trench-type isolation method as the standard CMOS process.

FIG. 7E is a sectional view illustrating the front end process in the trench-type isolation method as the standard CMOS process.

FIG. 7F is a sectional view illustrating the front end process in the trench-type isolation method as the standard CMOS process.

FIG. 7G is a sectional view illustrating the front end process in the trench-type isolation method as the standard CMOS process.

FIG. 7H is a sectional view illustrating the front end process in the trench-type isolation method as the standard CMOS process.

FIG. 7I is a sectional view illustrating the front end process in the trench-type isolation method as the standard CMOS process.

FIG. 7J is a sectional view illustrating the front end process in the trench-type isolation method as the standard CMOS process.

FIG. 7K is a sectional view illustrating the front end process in the trench-type isolation method as the standard CMOS process.

FIG. 7L is a sectional view illustrating the front end process in the trench-type isolation method as the standard CMOS process.

FIG. 8A is a sectional view illustrating an n-well process serving as an element isolation technique in a standard CMOS process.

FIG. 8B is a sectional view illustrating a p-well process serving as an element isolation technique in a standard CMOS process.

FIG. 8C is a sectional view illustrating a twin-well process serving as an element isolation technique in a standard CMOS process.

FIG. 8D is a sectional view illustrating a triple-well process serving as an element isolation technique in a standard CMOS process.

FIG. 9A is a sectional view showing part of a semiconductor device according to Example 1.

FIG. 9B is a circuit diagram of an imaging element by using the semiconductor device according to Example 1.

FIG. 10A is a diagram showing the relationship between the height of the Schottkey barrier and the workfunction of a metal used for an electrode in the case where an epitaxial layer in Example 1 is a p-type semiconductor.

FIG. 10B is a diagram showing the relationship between the height of the Schottkey barrier and the workfunction of a metal used for an electrode in the case where an epitaxial layer in Example 1 is an n-type semiconductor.

FIG. 10C is a diagram showing the relationship between the Ge compound crystal mole fraction, the height of the Schottkey barrier, and the indirect band gap in the epitaxial layer in Example 1.

FIG. 11A is a sectional view illustrating a Schottkey barrier formation step of the semiconductor device in Example 1.

FIG. 11B is a sectional view illustrating a Schottkey barrier formation step of the semiconductor device in Example 1.

FIG. 11C is a sectional view illustrating a Schottkey barrier formation step of the semiconductor device in Example 1.

FIG. 11D is a sectional view illustrating a Schottkey barrier formation step of the semiconductor device in Example 1.

DESCRIPTION OF EMBODIMENTS

A method for manufacturing a semiconductor device according to an aspect of the present invention realizes a semiconductor device which is CMOS-compatible and which includes a Schottkey barrier for rectification and electromagnetic wave detection. For that purpose, an epitaxial layer is locally disposed just above a layer having the same composition and height as those of a specific layer formed by a standard CMOS process. The local epitaxial layer is a semiconductor layer formed by epitaxial growth of a material and constitutes a Schottkey barrier of a detection element to detect electromagnetic waves. The epitaxial layer is in the shape of islands in the in-plane direction of a Si substrate and is suitable for two-dimensional array detection elements because it is possible to two-dimensionally distribute on the substrate.

In this regard, in the present invention and the present specification, the term "the heights are the same" refers to that the upper surfaces thereof are present in the same plane parallel to a work surface of the substrate (usually one of two surfaces having the largest area). However, this need not apply in the case where the work surface of the substrate is, for example, stepwise and, therefore, is not flat.

The epitaxial growth is performed between the front end process (process to form an integrated structure including a transistor, a polysilicon resistance element, a MOS capacitative element, and the like) in the standard CMOS process and the back end process (process to carry out metal wiring between transistors and various elements). This is because an influence of a heat treatment employed for the epitaxial growth is not exerted on a configuration formed through the back end process, in which Al wiring, Cu wiring, and the like are employed, in the standard CMOS process. Specifically, the epitaxial growth is performed before the back end process and, therefore, degradation in the metal wiring formed in the back end process does not occur even when the heat treatment for the epitaxial growth is performed.

Consequently, it becomes possible to subject the epitaxial layer as part of the Schottkey barrier to a heat treatment at a maximum temperature employed in the standard CMOS process, for example, 1,000 degrees Celsius or higher and 1,100 degrees Celsius or lower employed in thermal oxidation or activation annealing after ion implantation. Temperatures at which impurities in CMOS do not diffuse can be employed. For example, 800 degrees Celsius or higher and 900 degrees Celsius or lower are employed.

In the case where the epitaxial growth is performed before the front end process, it is difficult to leave the epitaxial layer by the standard CMOS process. Even when the epitaxial layer is left, the epitaxial layer is oxidized by a thermal oxidation step to form the MOS and it is impossible to use the outermost surface thereof for the Schottkey barrier.

The Schottkey barrier is formed by adding a Schottkey metal to the outermost surface of such an epitaxial layer. The Schottkey barrier is used as a structure to obtain I-V (current-voltage) characteristics of a Schottkey barrier diode, although not limited to this. The Schottkey barrier may be used as a structure to obtain metal semiconductor field effect transistor (MESFET). Both have voltage regions in which a current increases nonlinearly with respect to voltage application and may be used for rectification and detection of electromagnetic waves.

As described above, the Schottkey barrier forming step is performed between the front end process and the back end process in the standard CMOS process and, thereby, the semiconductor device, in which the CMOS and the detection element are integrated on the Si substrate, is formed by using the standard CMOS process. That is, a CMOS-compatible semiconductor device having an affinity for the standard CMOS process is provided.

Consequently, according to the method for manufacturing a semiconductor device as an aspect of the present invention, the semiconductor device, in which the epitaxial layer disposed just above a layer having the same composition and height as those of a specific layer formed by the CMOS process is used as part of the Schottkey barrier, may be provided. The semiconductor device including the Schottkey barrier can be used for detecting, in particular, electromagnetic waves (hereafter may be simply referred to as "terahertz waves") containing at least part of frequency components in a frequency region from the millimeter wave band to the terahertz band (30 GHz or more and 30 THz or less).

The semiconductor device according to an aspect of the present invention may be used for an imaging element to detect terahertz waves and perform imaging and an image forming apparatus by using the imaging element. As a matter of course, semiconductor devices adaptable to electromagnetic waves with frequencies lower than the visible light region and the near-infrared region other than the terahertz waves and imaging elements and image forming apparatuses by using the same may be provided.

In addition, CMOS-compatible semiconductor device in which the characteristics of the Schottkey barrier can be designed may be obtained by employing the above-described configuration. For example, in the semiconductor device in which the epitaxial layer disposed just above a layer having the same composition and height as those of a specific layer formed by the CMOS process is used as part of the Schottkey barrier diode, an epitaxial layer containing materials other than Si may be integrated on the same substrate as the substrate of the CMOS.

The first example of the considered materials is silicon germanium (SiGe). The barrier potential is controlled by a Ge compound crystal. Consequently, it becomes possible to adjust the impedance, e.g., resistance and capacitance, of the Schottkey barrier, so that the condition of impedance-matching to, for example, the receiving antenna to receive electromagnetic waves may be adjusted.

The second example is a III-V compound semiconductor, e.g., gallium arsenide (GaAs) or indium phosphide (InP). The III-V compound semiconductor has relatively high mobility and, therefore, a Schottkey barrier diode and a MESFET operable in the higher frequency side in the frequency region from the millimeter wave band to the terahertz band may be provided. Also, a semiconductor having a relatively narrow band gap may be selected and typically, an operation at a low bias voltage is possible.

Also, the outermost surface of the epitaxial layer, which does not suffer plasma damage, e.g., dry etching, may be used as part of the Schottkey barrier. Furthermore, it is possible to modify the semiconductor surface. For example, a stable Schottkey barrier may be formed by subjecting surface dangling bonds to hydrogen termination.

In the manufacturing method according to the present embodiment, in which the Schottkey barrier forming step is included between the front end process and the back end process in the standard CMOS process, the material for the outermost layer of the semiconductor layer (epitaxial layer) and the material for a Schottkey metal serving as the electrode may be selected optionally.

As for the outermost layer of the epitaxial layer, lattice-mismatched semiconductor with a thickness less than or equal to the critical film thickness may be used. In the case where the material for the Schottkey metal is selected in such a way that the height of the Schottkey barrier is changed considerably, the Schottkey barrier may be formed by using either the n-type semiconductor or the p-type semiconductor. A conductivity type suitable for reduction in delay of the detection element or a conductivity type suitable for reduction in noise may be selected. There are severe limitations to usable lattice-mismatched semiconductor materials and electrode materials depending on the order of processes with heat treatments. However, the flexibility in the selection may be increased considerably through the manufacturing method according to the present invention.

The semiconductor device which has such effects and which is formed by using the standard CMOS process may be produced relatively inexpensively in spite of higher performance than ever. Also, the base is the Si substrate, where 200-mm and 300-mm wafers are distributed at present, so that an increase in the number of pixels of the image forming apparatus adaptable to electromagnetic waves in frequency bands lower than the visible light region and the near-infrared region is facilitated. The embodiments will be described below with reference to the drawings.

First Embodiment

A semiconductor device according to a first embodiment will be described with reference to FIG. 1. FIG. 1 is a sectional view showing an integrated structure which is part of the semiconductor device according to the present embodiment. The semiconductor device according to the present embodiment is obtained by carrying out metal wiring between transistors, Schottkey barrier diodes, and the like of the integrated structure shown in FIG. 1 through the back end process in the standard CMOS process. The configuration and a detailed manufacturing method of the semiconductor device will be described later.

The semiconductor device according to the present embodiment includes a detector element 101, a p-type MOS transistor (hereafter referred to as pMOS) 102, and an n-type MOS transistor (hereafter referred to as nMOS) 103. These constituents are arranged in an in-plane direction on a Si substrate (hereafter referred to as substrate) 11.

A CMOS according to the present embodiment is constructed from the pMOS 102, the nMOS 103, and the like on the substrate 11 and is used as an image forming apparatus to control Schottkey barrier diode arrays two-dimensionally arranged in large numbers on the substrate 11 and process signals.

Here, the pMOS 102 and nMOS 103 are produced by using the standard CMOS process. The standard CMOS process has some variations and the present embodiment is an example of an n-well process in a local oxidation of Si (LOCOS) method. That is, a field oxide films (thermal oxide films for LOCOS) 12 to isolate elements and n-wells 13 are included.

Each of the pMOS 102 and the nMOS 103 includes source and drain, thermal oxide films (gate oxide films) 122 and 132, and polysilicons 123 and 133 serving as the gate. The source and drain include impurity diffusion layers 121 and 131. The thermal oxide films for LOCOS 12 are disposed between the pMOS 102 and the nMOS 103 and between the nMOS 103 and the detection element 101 to isolate the individual elements.

The detection element 101 is constructed on the substrate 11 to detect terahertz waves and includes the Schottkey barrier diode. The detection element 101 includes two electrodes of an anode 113 and a cathode 114 and an epitaxial layer 112. A Schottkey barrier is formed by adding the anode 113 and the cathode 114 serving as Schottkey metals to the outermost surface of the epitaxial layer 112.

The epitaxial layer 112 is a semiconductor layer epitaxially grown just above an impurity diffusion layer 111 having the same composition and height as those of an impurity diffusion layer 121 in the source or drain of the pMOS 102. The epitaxial layer 112 is not limited to a single layer but may be a plurality of layers stacked.

In the present specification, the layers having the same composition and height on the substrate 11 are formed at the same time through the same steps in the CMOS process, although the places on the substrate 11 and the purposes are different from each other. In this regard, the term "form at the same time" does not necessarily refer to that the timings of formation of the individual layers are the same completely. That is, in formation of the semiconductor device, the layers having the same composition and height by performing the same step are assumed to be the layers having the same composition and height. That is, in the present embodiment, the impurity diffusion layer 111 formed at the same time with the impurity diffusion layer 121 or 131 formed for the purpose of forming the source or drain in the pMOS 102 is used as a seed layer to integrate diodes. As a result, the compositions of the impurity diffusion layers are the same within the range of in-plane distribution on the substrate 11, and the heights in the in-plane direction are the same within the range of the scale controllable by the same thermal oxidation step and etching step. In this case, the etching is predominant and even when the heights are the same, there is surface roughness on the order of, typically, several nanometers.

At the time of the epitaxial growth, the surrounding structure is in the state in which only silicon, e.g., the substrate 11 and polysilicons 123 and 133, and glass, e.g., the thermal oxide film for LOCOS 12 and the gate oxide films 122 and 132 serving as thermal oxide films, are present. The melting points of them are higher than the heat treatment temperature of the epitaxial growth, so that the surrounding structure has the resistance against the heat treatment at the time of the epitaxial growth. Consequently, the semiconductor device according to the present invention may be formed by using the front end process in the standard CMOS process and, therefore, may be called a CMOS-compatible semiconductor device.

The thus formed epitaxial layer 112 may be Si which lattice-matches the impurity diffusion layer 111 as a matter of course, although other materials may be employed. For example, it is possible to grow a crystal of GaAs having a lattice constant of 5.653 angstroms on the Si substrate 11 having a lattice constant of 5.430 angstroms by using a well-known technology. Also, lattice-mismatched SiGe or Ge, or GaAs through a SiGe buffer layer may be employed. The lattice constant of the material contained in the epitaxial layer 112 is preferably within the range of 5.430 angstroms or more and 5.653 angstroms or less because a good-quality epitaxial layer 112 is formed on the Si substrate 11.

In addition, as for the epitaxial growth, the place on the substrate 11, at which the growth occurs, may be selected on the basis of differences in the lattice constant, other properties, and the structure between the impurity diffusion layer 111 serving as a seed layer and other portions. It is possible that selectivity of non-growth region is ensured by using a masking material, and it is also possible to locally leave the epitaxial layer 112 just above the impurity diffusion layer 111. At this time, the selectivity is enhanced by adjusting the growth conditions (for example, the substrate temperature, the raw material ratio, the pressure, and the like).

As for the crystal growing method of the epitaxial growth, a chemical vapor deposition method (CVD method) or a metal-organic vapor phase epitaxy method (MOVPE method) may be selected. In the CVD method and the MOVPE method, small amounts of impurities may be mixed into the epitaxial layer, so that a molecular beam epitaxy method (MBE method) or the like including smaller amounts of impurities may be employed. In any event, conditions under which influences of heat and the like because of this epitaxial growth are not exerted on the element formed in the front end process may be selected.

After the epitaxial growth, Schottkey electrodes or ohmic electrodes serving as the anode 113 and the cathode 114 are added to the epitaxial layer 112 and, thereby, a diode structure is completed. The electrodes can be arranged on the outermost layer of the epitaxial layer 112.

In the present embodiment, the epitaxial layer 112 remains having an area smaller than the area of the impurity diffusion layer 111 serving as the seed layer. This is because an electric delay of terahertz wave in the diode is reduced. Meanwhile, the diode is of two electrodes on a surface type. The detection current passes in the vicinity of the anode and the cathode on the surface of the diode. Therefore, in the configuration, a noise can be small because the detection current does not pass easily through parts having incomplete lattice structures, most of which are present at the bottom portion of the epitaxial layer 112.

The formation is performed by using the front end process in the standard CMOS process. As a result, the thermal oxide films for LOCOS 12 are always located between the detection element 101 and the pMOS 102 and between the detection element 101 and the nMOS 103 and serve as element isolation structures in the in-plane direction. Furthermore, in the present embodiment, the impurity diffusion layer 111 is a p-type semiconductor, so that in the case where Si is selected for the epitaxial layer 112, element isolation from the pMOS 102, the nMOS 103, the Si substrate 11, and the like becomes possible by selecting the n-type, which is opposite to the p-type, as the conductive type.

The impurity diffusion layer 111 serving as the seed layer is not limited to the impurity diffusion layer 121 in the source or drain of the pMOS 102, but a modified example is also considered, wherein an n-type semiconductor having the same composition and height as those of the impurity diffusion layer 131 in the source or drain of the nMOS 103 is used. In that case, the same element isolation is possible by using a structure, in which an n-type semiconductor is grown after a p-type semiconductor is grown, as the epitaxial layer. The same structure may be formed by using ion implantation.

The semiconductor device according to the present invention is CMOS-compatible and the characteristics of the Schottkey barrier may be designed.

The configuration according to the present invention is an example in which the step to expose the seed layer 111 is relatively easy and the structure is simple In the present embodiment, the epitaxial layer 112 is grown just above the impurity diffusion layer 111 formed in the same step and at the same time with formation of the impurity diffusion layer 121. All the impurity diffusion layers 111, 121, and 131 are formed by subjecting the substrate 11 surface to ion implantation and activation annealing. Therefore, the impurity diffusion layer 111 before the epitaxial growth is part of the substrate 11 used in the front end process, and the epitaxial layer 112 is formed on the substrate 11 surface. However, even in the case where the semiconductor species of the epitaxially grown semiconductor layer (epitaxial layer) 112 is the same as the species of the surface of the substrate 11, the epitaxial layer 112 has properties in which the film quality, e.g., the impurity concentration and the defect density, are substantially different depending on the growing method and the condition.

That is, the substrate 11 surface follows the properties on the basis of a substrate formation method, e.g., a Czochralski method (CZ method) or a float zone technology method (FZ method). On the other hand, the epitaxial layer 112 includes impurities, e.g., carbon, contained in the raw material gas in the case of the CVD method or MOVPE method or impurities remaining in a vacuum chamber in the case of the MBE method.

Therefore, the layer having the same composition and height as those of the impurity diffusion layer 121, that is, the semiconductor layer (epitaxial layer) 112 grown on the impurity diffusion layer 111 is distinguishable from the semiconductor layer of the substrate 11 on the basis of the analysis and the electric characteristics. In many cases where local epitaxial growth is performed, impurities, e.g., oxygen, and an amorphous layer may be present at the interface between the epitaxial layer 112 and the seed layer (impurity diffusion layer) 111. Consequently, the element produced by the manufacturing method according to the present invention has a structure specific to the manufacturing method.

Second Embodiment

A semiconductor device according to a second embodiment will be described with reference to FIG. 2. FIG. 2 is a sectional view showing an integrated structure which is part of the semiconductor device according to the present embodiment. The semiconductor device according to the present embodiment is obtained by carrying out metal wiring between transistors, diodes, and the like included in the integrated structure of the semiconductor device shown in FIG. 2 through the back end process in the standard CMOS process. In this regard, the configuration and a manufacturing method of the semiconductor device will be described later. The explanations of the same portions as those in the first embodiment will not be provided.

The semiconductor device according to the present embodiment includes a detector element 201, a pMOS 102, and an nMOS 103. In the present embodiment, the detection element 201 is constructed on a substrate 11 and is a detection element to detect electromagnetic waves from the millimeter wave band to the terahertz band, as in the first embodiment. The detection element 201 includes two electrodes of an anode 213 and a cathode 214 and an epitaxial layer 212. A Schottkey barrier is formed by adding the anode 213 and the cathode 214 serving as Schottkey metals to the outermost surface of the epitaxial layer 212.

In the present embodiment, the epitaxial layer 212 is disposed on the surface of a region, in the substrate 11, having the same composition and height as those of a channel region, in the substrate 11, just below a gate oxide film 132 of the nMOS 103 by epitaxial growth. The region to be provided with the epitaxial layer 212 may be just above the region, in the substrate 11, having the same composition and height as those of a channel region, in the substrate 11, just below a gate oxide film 122 of the pMOS 102. The epitaxial layer 212 is not limited to a single layer but may be a plurality of layers stacked.

In the present embodiment, the regions having the same composition and height refer to regions which are formed through the same steps at the same time in the CMOS process, although the places on the substrate 11 and the purposes are different from each other. As a result, the composition of the channel region, in the substrate 11, just below the gate oxide film 132 is the same as the composition of the channel region, in the substrate 11, just below the gate oxide film, which has been removed in FIG. 2, within the range of in-plane distribution on the substrate 11, and the heights in the in-plane direction are the same within the range of the scale controllable by the same thermal oxidation step. In this regard, the thermal oxidation step of the gate is very precise and, typically, it is possible to perform control within 1 nanometer or less.

As for the Si substrate 11 surface according to the present embodiment, a region formed for the purpose of forming the channel region in the nMOS is used as the seed layer to integrate the detection element 201. Therefore, the substrate 11 surface in the state of having been subjected to the same process as with the gate oxide film 132 serves as the seed layer for the growth.

As in the first embodiment, at the time of growth, the surrounding structure is in the state in which only silicon and glass are present. The melting points of them are very high, so that the resistance to the heat treatment in the epitaxial growth is exhibited. Consequently, it may be said that the semiconductor device by using the integrated structure shown in FIG. 2 is a CMOS-compatible semiconductor device which is formed by using the standard CMOS process, that is, which has affinity for the standard CMOS process.

As a result, the thermal oxide films for LOCOS 12 are located between the detection element 201 and the pMOS 102 and between the detection element 201 and the nMOS 103 and serve as element isolation structures in the in-plane direction. Furthermore, in FIG. 2, the Si substrate 11 is a p-type semiconductor, so that in the case where Si is selected for the epitaxial layer 212, element isolation from the pMOS 102, the nMOS 103, the Si substrate 11, and the like becomes possible by selecting the n-type, which is opposite to the p-type, as the conductive type. A modified example is also considered, wherein an n-well in the pMOS is used as the Si substrate 11 serving as the seed layer. In that case, the same element isolation is possible by growing a p-type semiconductor on an epitaxial layer and, thereafter, growing an n-type semiconductor to form the epitaxial layer 212.

In the configuration of the present embodiment, the region, in the substrate, having the same composition and height as those of the channel region, in the substrate, just below the gate oxide film of the nMOS or pMOS is used as the seed layer in the epitaxial growth. This seed layer is configured to obtain a best surface state with reduced defects and the like but is an example of a structure with relative difficulty of performing the exposure step because there is a need to remove a polysilicon gate and a gate thermal oxide film.

In the exposure step, for example, a portion excluding polysilicon gate (not shown in the drawing) in the nMOS concerned is masked by patterning through photolithography or the like and, thereafter, polysilicon (not shown in the drawing) and the thermal oxide film just below it are removed by using wet etching. As for an etchant, a mixed solution containing hydrofluoric acid and nitric acid may be used, where etching is inhibited by low-concentration impurity-doped single crystal silicon. At that time, gate side-wall insulating films 215 may be used as side-etching inhibition structures. However, the gate side-wall insulating films 215 are unnecessary for the present configuration and, therefore, may be removed thereafter.

Meanwhile, an image forming apparatus by using this has the same configuration as the configuration shown in FIG. 5 through the back end process in the CMOS process, and the detailed explanation will be provided later. In the present embodiment, the epitaxial layer 212 is grown just above the region, in the substrate 11, formed at the same time through the same steps as the steps to form the channel region, in the substrate 11, just below the gate oxide film 132. Therefore, the region on which the epitaxial growth is performed is the channel region, is part of the substrate 11 used in the front end process, and is the surface.

As with the first embodiment, even in the case where the semiconductor species of the epitaxially grown semiconductor layer (epitaxial layer) 122 is the same as the species of the substrate surface 11, the epitaxial layer 122 has properties in which the film quality, e.g., the impurity concentration and the defect density, are substantially different depending on the growing method and the condition.

The semiconductor device according to the present invention is CMOS-compatible and the characteristics of the Schottkey barrier may be designed.

Third Embodiment

A semiconductor device according to a third embodiment will be described with reference to FIG. 3. FIG. 3 is a sectional view showing part of an integrated structure of the semiconductor device according to the present embodiment. The semiconductor device according to the present embodiment is obtained by carrying out metal wiring between transistors, diodes, and the like included in the integrated structure of the semiconductor device shown in FIG. 3 through the back end process in the standard CMOS process. In this regard, the configuration and a manufacturing method of the semiconductor device will be described later. The explanations of the same portions as those in the above-described embodiments will not be provided.

The semiconductor device according to the present embodiment includes a detector element 301, a pMOS 102, and an nMOS 103. In the present embodiment, the detection element 301 is constructed on a substrate 11 and is a detection element to detect electromagnetic waves from the millimeter wave band to the terahertz band, as in the first embodiment. The detection element 301 includes two electrodes of an anode 313 and a cathode 314 and an epitaxial layer 312. A Schottkey barrier is formed by adding the anode 313 and the cathode 314 serving as Schottkey metals to the outermost surface of the epitaxial layer 312.

In the present embodiment, the detection element 301 is constructed on a substrate 11 and is a detection element to detect electromagnetic waves from the millimeter wave band to the terahertz band, as in the first embodiment. In the present embodiment, the epitaxial layer 312 is epitaxially grown just above a region, in the substrate 11, having the same composition and height as those of a region, in the substrate 11, just below an element isolation oxide film 12 formed between the pMOS 102 and the nMOS 103. The epitaxial layer 312 is not limited to a single layer but may be a plurality of layers stacked.

In the present embodiment as well, the regions having the same composition and height refer to regions which are formed through the same steps at the same time in the CMOS process, although the places on the substrate and the purposes are different from each other. As a result, the compositions of the regions, in the substrate 11, just below the element isolation oxide films 12 are the same within the range of in-plane distribution on the substrate 11, and the heights in the in-plane direction are the same within the range of the scale controllable by the thermal oxidation step (LOCOS method) or the etching step (trench-type isolation method). In any event, in this case, surface roughness of several nanometers is unavoidable Impurities are mixed into the substrate 11 through the above-described steps and, thereby, the composition of the outermost layer is slightly different from the composition of the portion in the substrate 11.

As for the Si substrate 11 surface according to the present embodiment, a region just below the thermal oxide film for LOCOS 12 to perform element isolation is used as the seed layer to integrate the detection element 301. Therefore, the substrate 11 surface exposed by removing the thermal oxide film for LOCOS 12 serves as the seed layer for the epitaxial growth.

As in the first embodiment, at the time of growth, the surrounding structure is in the state in which only silicon and glass are present. The melting points of them are very high, so that the resistance to the heat treatment in the epitaxial growth is exhibited. Consequently, it may be said that the semiconductor device by using the integrated structure shown in FIG. 3 is a CMOS-compatible semiconductor device which is formed by using the front end process in the standard CMOS process and which has affinity for the standard CMOS process.

As a result, the thermal oxide films for LOCOS 12 are located between the detection element 301 and the pMOS 102 and between the detection element 301 and the nMOS 103 and serve as element isolation structures in the in-plane direction. Furthermore, in the present embodiment as well, the substrate 11 is a p-type semiconductor, so that in the case where Si is selected for the epitaxial layer 312, element isolation from the pMOS 102, the nMOS 103, the substrate 11, and the like becomes possible by selecting the n-type, which is opposite to the p-type, as the conductive type. A modified example is also considered, wherein an n-well in the pMOS 102 is used as the substrate 11 serving as the seed layer. In that case, the same element isolation is possible by using a configuration, in which a p-type semiconductor is grown and, thereafter, an n-type semiconductor is grown, as the epitaxial layer 312.

In the configuration of the present embodiment, the region, in the substrate 11, having the same composition and height as those of the region, in the substrate 11, just below the element isolation oxide film 12 formed between the pMOS 102 and the nMOS 103 is used as the seed layer in the epitaxial growth. In this case, a good surface state with reduced defects is obtained, although the state in the second embodiment is not reached. The exposure step to remove the oxide film 12 and expose the Si substrate 11 surface is relatively easy and the structure is simple, although those in the first embodiment are not reached.

However, in comparison with the above-described embodiments, the area of the detection element 301 on the substrate 11 may be saved. This is because part of the thermal oxide film for LOCOS 12 by the LOCOS method, in which the area becomes relatively large easily, is also used as the region for forming the detection element 301. Therefore, the present embodiment is convenient to make a pixel finer.

Meanwhile, an image forming apparatus by using this has the same configuration as the configuration shown in FIG. 5 through the back end process in the CMOS process and, therefore, the explanation will not be provided.

In the present embodiment, the epitaxial layer 312 is grown just above the surface of the region, which is to be provided with the detection element 301 on the Si substrate 11, formed at the same time with formation of the substrate 11 surface just below the element isolation oxide film 12 disposed between the pMOS 102 and the nMOS 103. Therefore, the surface concerned before the epitaxial growth is the substrate surface used in the front end process. In this regard, even in the case where the semiconductor species of the epitaxially grown semiconductor layer is the same as the species of the above-described substrate surface, the semiconductor layer has properties in which the film quality, e.g., the impurity concentration and the defect density, are substantially different depending on the growing method and the condition.

The semiconductor device according to the present invention is CMOS-compatible and the characteristics of the Schottkey barrier may be designed.

Fourth Embodiment

A semiconductor device according to a fourth embodiment will be described with reference to FIG. 4. FIG. 4 is a sectional view showing part of an integrated structure of the semiconductor device according to the present embodiment. The semiconductor device according to the present embodiment is obtained by carrying out metal wiring between transistors, MESFETs, and the like included in the integrated structure of the semiconductor device shown in FIG. 4 through the back end process in the standard CMOS process. The configuration and a manufacturing method of the semiconductor device according to the present embodiment will be described later. The explanations of the same configurations as those in the above-described embodiments will not be provided.

The semiconductor device according to the present embodiment includes a detector element 401, a pMOS 402, and an nMOS 403. In the present embodiment, the detection element 401 is a MESFET to detect terahertz waves. The detection element 401 includes three electrodes of a source 413, a gate 416, and a drain 414 and an epitaxial layer 412 and constitutes a Schottkey barrier. The epitaxial layer 412 is a semiconductor layer and is not limited to a single layer but may be a plurality of layers stacked.

In the case of the Schottkey barrier diode, typically, the Schottkey barrier is disposed just below the anode with an n-type semiconductor or just below the cathode with a p-type semiconductor. However, in the case of the MESFET, the Schottkey barrier is disposed just below the gate.

The CMOS is configured to include the pMOS 402, the nMOS 403, and the like on the substrate 41 and is used for controlling MESFET arrays arranged in large numbers in the in-plane direction on the Si substrate 41 and processing signals, as an image forming apparatus.

The pMOS 402 and the nMOS 403 are produced by using the standard CMOS process. The present embodiment is an example of a twin-well process in the trench-type isolation method. That is, the semiconductor device includes a field oxide films (CVD oxide films) 42 for element isolation, n-wells 43, and a p-well 44. The conductive type of the substrate 41 is either p-type or n-type.

The pMOS 402 and the nMOS 403 include impurity diffusion layers 421 and 431, respectively, serving as the source and drain, thermal oxide films (gate oxide films) 422 and 432, respectively, and polysilicons 423 and 433, respectively, serving as the gates. Oxide films 42 formed by the CVD method are disposed between the pMOS 402, the nMOS 403, and the detection element 401 to isolate the individual elements.

In the present embodiment by using the trench-type isolation method as well, as in the first embodiment, the epitaxial layer 412 is epitaxially grown just above an impurity diffusion layer 411 having the same composition and height as those of the impurity diffusion layer 421 in the source or drain of the pMOS 402. Alternatively, the epitaxial layer 412 may be grown just above the impurity diffusion layer 411 having the same composition and height as those of the impurity diffusion layer 431 in the source or drain of the nMOS 403.

As is explained in the first embodiment, in the case where the epitaxial layer 412 is Si, the element isolation is possible when the epitaxial layer 412 includes a layer having a conductive type different from the conductive type of the impurity diffusion layer 411. The same goes for the case where SiGe is used as the epitaxial layer 412.

In the case where the epitaxial layer 412 is GaAs or InP, the element isolation is easy when a material, e.g., aluminum gallium arsenide (AlGaAs) or indium gallium arsenide (InGaAs), having a band gap larger than the band gaps of them is adopted. As for the III-V compound semiconductor, a technology to increase the resistivity by compensating for carriers with deep introduction of impurities or the like has been advanced, and the element isolation is possible without using a material having a large band gap.

In the trench-type isolation method, the configuration as in the second embodiment may be considered. That is, the epitaxial layer 412 may be epitaxially grown on the surface of a region, in the substrate 41, having the same composition and height as those of a channel region, in the substrate 41, just below the thermal oxide film 422 or 432 of the pMOS 402 or nMOS 403. As in the second embodiment, with respect to the seed layer 41 in the epitaxial growth, this configuration obtains a good surface state with reduced defects and the like.

Also, as in the third embodiment, the epitaxial layer 412 may be grown on the surface of a region, in the substrate 41, having the same composition and height as those of a region, in the substrate 41, just below the oxide film 42. As for the Si substrate 41 surface, on the p-well 43 may be selected or on the n-well 44 may be selected. In this case, as with the third embodiment, the oxide film 42 may also be used as the region for forming the MESFET 401 and, therefore, the present embodiment is convenient to make a pixel finer.

As in the LOCOS method, in the standard CMOS process by using the trench-type isolation method, at the time of epitaxial growth, the surrounding structure is in the state in which silicon and glass, e.g., the CVD oxide film 42 and the thermal oxide films 422 and 432, are present.

Furthermore, the source, the gate, the drain of each of the pMOS 402 and the nMOS 403 formed by the CMOS process according to the present embodiment are provided with the silicide 424 or silicide 434 to reduce the contact resistance in contact with a metal used in the back end process. This is a compound crystal of Si and a metal and typical examples include tungsten silicide (WSi), titanium silicide (TiSi), cobalt silicide (CoSi), and nickel silicide (NiSi). The melting points of them are very high as compared with the temperature of the heat treatment in the epitaxial growth.

That is, each structure formed by using the front end process in the standard CMOS process according to the present embodiment has the resistance to the heat treatment for the epitaxial growth and physical stability. Therefore, the semiconductor device according to the present embodiment is CMOS-compatible and the characteristics of the Schottkey barrier may be designed.

In the present embodiment, after the epitaxial growth, the MESFET 401 structure is completed by adding a gate electrode 416, a source electrode 413, and a drain electrode 414 to the resulting epitaxial layer. The gate electrode can be arranged on the outermost layer of the epitaxial layer 412.

Meanwhile, an image forming apparatus by using this has the same configuration as the configuration shown in FIG. 5 through the back end process in the standard CMOS process and, therefore, the explanation will not be provided.

Fifth Embodiment

A semiconductor device according to a fifth embodiment will be described with reference to FIG. 5. FIG. 5 is a sectional view showing part of the semiconductor device according to the present embodiment. Specifically, the integrated structure which is part of the semiconductor device according to the first embodiment is subjected to the back end process in the standard CMOS process, and a pixel including at least a detection element and a circuit to control detection signals and process the signals is illustrated. The explanations of the same configurations as those in the above-described embodiments will not be provided.

The semiconductor device according to the present embodiment includes a detection circuit 1001 (hereafter referred to as "circuit 1001") and a control and signal processing circuit 1002 (hereafter referred to as "circuit 1002").

The circuit 1001 is a portion to detect terahertz waves and includes a detection element 101 and antennas formed from metal components 1621 and 1622. The detection element 101 is electrically connected to the antennas 1621 and 1622 through vias 151 and 161 and electrodes 113 and 114.

The antennas 1621 and 1622 have the functions of capturing terahertz waves propagating in a free space and converting to a current and a voltage close to the impedance of a Schottkey barrier diode of the detection element 101. As for the antennas 1621 and 1622 in the present embodiment, the planar antenna pattern is formed from second metal wiring 162. As a matter of course, an antenna by using two metal layers composed of the first metal wiring 152 and the second metal wiring 162 may be employed.

The vias 151 and 161 are a metal and have the function of transmitting high-frequency electric signals from the antennas 1621 and 1622 to the detection element 101 with low losses. The detection element 101 has a function of generating detection signals proportional to the intensity of terahertz waves received by the antennas 1621 and 1622 on the basis of rectification of the high-frequency electric signals. The detection signals are taken out through the first metal wiring 152 on a first interlayer insulating film 15 or the second metal wiring 162 on a second interlayer insulating film 16 to the circuit 1002.

The circuit 1002 is an amplifier circuit and is constructed by electrically connecting the pMOS 102 and the nMOS 103 through the vias 151 and 161, the first metal wiring 152, and the second metal wiring 162. Furthermore, third metal wiring and fourth metal wiring may be used. In the present embodiment, the cross-sectional structure of only the CMOS portion of the circuit 1002 in which the pMOS 102 is connected to the nMOS 103 is shown. However, the amplifier circuit may be constructed in association with a resistance element, a capacitative element, and the like on the substrate 11. Such a circuit configuration may be used for amplifying electric signals from the circuit 1001.

The circuit 1002 is able to stop the output of signals at the command of an outside circuit and, therefore, is allowed to have a role of a pixel switch. Consequently, the circuit 1002 may be used for control to access and address an optional pixel in an imaging element having a large number of pixels, e.g., 100 pixels per line. For these reasons, the circuit 1002 is indispensable to the semiconductor device according to the present embodiment.

As shown in FIG. 5, in the semiconductor device according to the present embodiment, the circuit 1001 and the circuit 1002 are integrated at adjacent places on the same substrate 11. Usually, foreign noises overlap the detection signals from the circuit 1001 easily, and this occurs considerably as the length of connection wiring between the circuit 1001 and the circuit 1002 increases. Therefore, in the configuration according to the present embodiment, the circuit 1001 can be connected to the circuit 1002 in the shortest distance, so that the S/N ratio of the detection signal is excellent.

For example, according to the sampling theorem, an appropriate size of one side of a pixel is a half-wave length, so that the size of the pixel at 1 THz is 150 micrometers in the air. The adjacently integrated circuit 1001 and the circuit 1002 can be connected easily in the distance less than or equal to a half-wave length in order to ensure excellent S/N.

In addition, the configuration to reduce foreign noises is easily constructed. For example, in the case where a low-floor level wiring, e.g., the first metal wiring 152, is used as the connection wiring, a high-floor level wiring, e.g., the second metal wiring 162, may be used as a shielding plate. It is effective to enhance a shielding effect by connecting between the second metal wiring 162 serving as the shielding plate and the substrate 11 through the vias 151 and 161. In any event, construction of the configuration capable of reducing foreign noises is difficult unless integration is performed on the same substrate 11.

At the time of carrying out of the metal wiring between transistors and various elements, the detection element 101, which has been subjected to a heat treatment, and silicon, e.g., the substrate 11 and polysilicons 123 and 133, are present in the surrounding structure. Also, glass, e.g., the thermal oxide film for LOCOS 12 and the thermal oxide films 122 and 132, which have been formed in the front end process in the CMOS process, are present. In the back end process in the standard CMOS process, a material accompanied with a heat treatment at a temperature lower than the temperatures experienced by such structures is adopted.

For example, as for the interlayer insulating films 15 and 16, a plasma CVD oxynitride film, a tetra ethyl ortho silicate (TEOS) film, or the like is selected. The film formation of them may be performed at a temperature sufficiently lower than the temperature of the thermal oxide film. As for the vias 151 and 161, a CVD metal or a plating metal is selected. The CVD-W method may fill the via with tungsten (W) by a heat treatment at about 400 degrees Celsius. At present, a Cu damascene method may be selected, where a via is filled with Cu without being accompanied with a special heat treatment.

As for the metal wiring 152 and 162, relatively inexpensive, high-electrical conductivity Al, dual damascene method-compatible Cu, or the like is selected. Therefore, it may be said that it is possible to apply the back end process in the standard CMOS process to the semiconductor device according to the present embodiment.

In this regard, for the purpose of defining terms, an example of the front end process in the standard CMOS process will be described with reference to FIG. 6A to FIG. 6K and FIG. 7A to FIG. 7L. FIG. 6A to FIG. 6K are sectional views illustrating an example of the front end process in a LOCOS method as the standard CMOS process. FIG. 7A to FIG. 7L are sectional views illustrating an example of the front end process in the trench-type isolation method as the standard CMOS process.

The steps in the LOCOS method include the process shown in FIG. 6A to FIG. 6K. To begin with, a Si substrate is prepared, and cleaning of impurities distributed on the substrate surface (FIG. 6A), surface thermal oxidation to form a gate thermal oxide film (FIG. 6B), and ion implantation and activation annealing to form an n-well (FIG. 6C) are performed. Thereafter, film formation of a nitride (SiN) film (FIG. 6D), nitride film etching to form a bird's peak pattern (FIG. 6E), and formation of a field oxide film (thermal oxide film for LOCOS, SiO), which is the largest feature of the LOCOS method, (FIG. 6F) are performed.

Subsequently, as necessary, ion implantation and activation annealing to determine the threshold value voltage Vth of the pMOS and the nMOS (FIG. 6G) is performed and, then, film formation and etching of polysilicon serving as a gate are performed, so that the step shown in FIG. 6H is completed. Ion implantation and activation annealing to form impurity diffusion layers serving as the source or the drain of the pMOS and the nMOS are performed and, thereby, the configuration shown in FIG. 6I is formed. Film formation of the CVD oxide film (SiO) of the gate side-wall insulating film (FIG. 6J) and a step to expose the contact and, at the same time, form the gate side-wall insulating film (FIG. 6K) are performed, so that the front end process is completed.

The front end process in the trench-type isolation method includes the process shown in FIG. 7A to FIG. 7L. To begin with, a Si substrate is prepared, and cleaning of impurities distributed on the substrate surface (FIG. 7A), film formation of an oxide film and film formation of a nitride film to protect the substrate surface (FIG. 7B), and etching to form a trench pattern by using the nitride film as a mask (FIG. 7C) are performed.

Thereafter, the step shown in FIG. 7D is performed by film formation of a CVD oxide film (SiO) and the like and chemical mechanical polishing (CMP) to smooth the surface. Subsequently, the nitride film (SiN) and the oxide film (SiO) are etched (FIG. 7E), so that a trench-type isolation structure, which is the largest feature of the trench-type isolation method, is formed by this method on the basis of shallow trench isolation (STI), where the trench is filled with the CVD oxide film. Then, ion implantation and activation annealing to form an n-well (FIG. 7F) are performed.

As necessary, cleaning on the substrate surface is further performed, a gate thermal oxide film is formed by performing surface thermal oxidation (FIG. 7G), and film formation and etching of polysilicon serving as a gate (FIG. 7H) are performed. Ion implantation and activation annealing to form lightly doped drain (LDD) structures in the source and drain of the pMOS and the source and drain of the nMOS (FIG. 7I) are performed. Furthermore, formation of a gate side-wall insulating film (FIG. 7J) and ion implantation and activation annealing to form impurity diffusion layers serving as the source and drain of the pMOS and the source and drain of the nMOS (FIG. 7K) are performed. Subsequently, siliciding is performed, where in order to improve contact, Ti, Co, Ni, and the like are brought into contact and a heat treatment is performed, (FIG. 7L), so that the front end process is completed.

In this regard, the ion implantation and the activation annealing to determine the threshold value voltage Vth, the step to form the LDD structure, and the siliciding step, as shown in FIG. 7L, are steps to improve the functionality in association with the finer design rule of the CMOS and are not indispensable. Such steps may be incorporated into both the LOCOS method and the trench-type isolation method. Likewise, for example, the CMP step shown in FIG. 7D is not indispensable and may be replaced with a surface smoothing step on the basis of a previously known etch back method.

A step to form pre metal dielectric (PMD), which is the following step in the CMOS process, may be or may not be included in the front end process in the present specification. This is because typically, SiO, phosphorus glass (PGS), or the like is selected as the material for the PMD and, as a result, the resistance to the heat treatment of epitaxial growth and the physical stability are exhibited.

Variations of element isolation techniques in the front end process in the CMOS process are shown in FIG. 8A to FIG. 8D. FIG. 8A shows an n-well process to form an n-well 83 on a p-type Si substrate 81 by an ion implantation method, diffusion method, or the like. FIG. 8B shows a p-well process to form a p-well 84 on an n-type Si substrate 81. FIG. 8C shows a twin-well process to form both the n-well 83 and the p-well 84 on the substrate 81. FIG. 8D shows a triple-well process to form a well 85 having a conductive type opposite to the conductive type of the substrate and both the n-well 83 and the p-well 84 on the p-type substrate 81.

Each of the LOCOS method and the trench-type isolation method, which are the standard CMOS processes, has eight variations on the basis of only the above-described combinations. However, the standard CMOS process in the present specification is not limited to them.

For example, all the following processes, in the case where it is possible to optionally change the order of steps to form the same structure, CMOS processes on the basis of such changes in the order of steps, in the case where there are alternatives to the steps to form the same structure, CMOS processes on the basis of such substitution of the steps, CMOS processes in which steps to form structures effective in enhancing the functionality but not indispensable are added or omitted, CMOS processes in which steps to form a resistance element or a MOS capacitative element by using an impurity diffusion layer or polysilicon on the same substrate as with the pMOS or nMOS are added, and CMOS processes in which steps, e.g., substrate cleaning or surface treatment, not accompanied with a structure are added or omitted, and combinations thereof are considered to be the standard CMOS process in the present specification. Also, it is considered that the same goes for BiCMOS processes in which bipolar transistors adopting the above-described CMOS processes and the CMOS are integrated.

As described above, the semiconductor device according to the present embodiment is CMOS-compatible and the characteristics of the Schottkey barrier may be designed.

A specific imaging element will be described below with reference to the example.

Example 1

In the present example, an imaging element by using the semiconductor device according to the above-described embodiment will be specifically described. FIG. 9A is a sectional view of a semiconductor device which is part of the imaging element according to the present example. FIG. 9B shows a circuit diagram of the imaging element in which such structures are arranged in a two-dimensional array and any pixel is able to be accessed optionally. The semiconductor device included a detection circuit 9001 (hereafter referred to as "circuit 9001") and a control and signal processing circuit 9002 (hereafter referred to as "circuit 9002"). The circuit 9001 included a detection element 901 and antennas formed from metal components 9621 and 9622. The detection element 901 was electrically connected to the antennas 9621 and 9622 through vias 951 and 961 and two electrodes 913 and 914. The circuit 9002 was an amplifier circuit and was constructed by electrically connecting the pMOS 902 and the nMOS 903 through the vias 951 and 961, the first metal wiring 952, and the second metal wiring 962. In addition, third metal wiring and fourth metal wiring may be used. These configurations are the same as the configuration of the semiconductor device according to the fifth embodiment and, therefore, the detailed explanations will not be provided.

In the present example, an 8-inch Si substrate having a diameter of 200 mm was used as a substrate 91. For example, a die (semiconductor device) with the number of pixels of 150 by 200, where one pixel is 0.6 mm square, was obtained by adopting the 8-inch Si substrate. A high-resistivity substrate 91 was used, which had a resistivity of 20 ohm centimeter or more and which was produced by a MCZ method, so that absorption of terahertz waves by the substrate 91 was reduced.

The detection element 901 was a Schottkey barrier diode (hereafter referred to as diode) including an epitaxial layer 912, a Schottkey electrode 913, and an ohmic electrode 914. An n-type SiGe compound crystal semiconductor was used as the outermost surface of the epitaxial layer 912. The epitaxial layer 912 was configured to include a high-concentration doped Si layer (first layer) 9121, a high-concentration doped $Si_{0.86}Ge_{0.14}$ layer (second layer) 9122, and a low-concentration doped $Si_{0.86}Ge_{0.14}$ layer (third layer) 9123 sequentially from the substrate 91 side.

The first layer 9121 had an n-type carrier concentration of 2 by $10^{19}$ cm$^{-3}$ and a thickness of 500 nm. The second layer 9122 had an n-type carrier concentration of 2 by $10^{19}$ cm$^{-3}$ and a thickness of 15 nm. The third layer 9123 had an n-type carrier concentration of 5 by $10^{17}$ cm$^{-3}$ and a thickness of 60 nm.

The first layer 9121 also served as a buffer layer and, therefore, a relatively thick layer was used. This is because in the case where the surface of the seed layer was not perfect, the most lower portion of the epitaxial layer 912 did not become a perfect crystal easily. In the present example, a region, in the substrate 91, having the same composition and height as those of a channel region, in the silicon substrate 91, just below a gate oxide film of the pMOS 902 or nMOS 903 was used as the seed layer.

The second layer 9122 and the third layer 9123 were lattice-mismatched systems relative to the substrate 91. It was well known that dislocation, misfit, and the like of these layers were able to be reduced by using a low-temperature epitaxial growth technology. In this regard, selection of 1 by $10^{17}$ cm$^{-3}$ or more and 1 by $10^{19}$ cm$^{-3}$ or less as the carrier concentration of the third layer 9123 was convenient for forming the Schottkey barrier structure. The third layer 9123 was brought into contact with the Schottkey electrode 913 and, thereby, a Schottkey barrier was formed on the semiconductor 9123 side included in the epitaxial layer 912.

The ohmic electrode 914 was brought into electrical contact with the high-concentration doped layers 9121 and 9122 through a high-concentration ion implant region 9124. In the present example, a Ti metal (the thickness was 200 nm) was used as the material for the Schottkey electrode 913 and the ohmic electrode 914. In this manner, the detection element 901 was constructed.

The Ge compound crystal mole fraction in the low-concentration doped layer 9123 of the SiGe epitaxial layer 912 and the magnitude of the barrier potential when the material for the Schottkey electrode 913 was changed will be described. An evaporation method was used for film formation of Ti, Al, Ni, and Pd serving as the Schottkey electrode 913 in order to reduce surface damage of the SiGe epitaxial layer 912.

To begin with, the magnitude of the barrier potential when the material for the Schottkey electrode 913 was changed will be described. FIG. 10A and FIG. 10B are diagrams showing the relationship between the Schottkey barrier height phi b and the metal workfunction of the metal used for the electrode.

In the case where the epitaxial layer 912 containing SiGe was a p-type semiconductor, the Schottkey barrier height phi b had the property of being decreased as the metal workfunction increased, as shown in FIG. 10A. In the case of an n-type semiconductor, the Schottkey barrier height exhibited the property of being increased as the metal workfunction increased, as shown in FIG. 10B. In these plots, an I-V (current-voltage) method was used for extraction of the Schottkey barrier height phi b. The value of the metal workfunction was extracted from the table described in WALTER H. KOHL, "Materials and Techniques for ELECTRON TUBES", p. 526.

FIG. 10C is a diagram showing the relationship between the degree of compound crystal of Ge in the epitaxial layer 912 containing SiGe, the Schottkey barrier height phi b, and the indirect band gap Eg. FIG. 10C also shows that the Schottkey barrier height phi b is able to be adjusted by the degree of compound crystal of Ge. In particular, FIG. 10C shows an example of p-type semiconductor. The Ge compound crystal mole fraction is increased and the indirect band gap Eg is reduced because of SiGe, so that in accordance with the tendency, the Schottkey barrier height phi b decreases.

One method for detecting terahertz waves, where detection with low noise and high sensitivity are required, is to realize a zero bias operation (operation point is 0 V and 0 A) of the detection element 901. For that purpose, the Schottkey barrier height phi b is preferably 0.4 eV or less, and desirably 0.1 eV or more and 0.3 eV or less. Therefore, p-type semiconductors Si and SiGe can be combined with a Schottkey metal of Ni having a workfunction of 4.6 eV to Pd having a workfunction of 5.0 eV, and n-type semiconductors Si and SiGe can be combined with a Schottkey metal of Ti having a workfunction of 3.9 eV to Al having a workfunction of 4.2 eV.

In the present example, the circuit 9001 was constructed by connecting the detection element 901 to the antennas 9621 and 9622. A well-known log-periodic antenna independent of frequency was used for the antennas 9621 and 9622.

In the present configuration, the detection element 901 was formed into the shape of islands. The size of the island was specified to be about 50 square micrometers or less to detect electromagnetic waves in the frequency band of 0.5 THz or more and 3 THz or less, and one side of the epitaxial layer 912 was designed to measure about 7 micrometers. One side of the channel serving as the seed layer of the epitaxial layer 912 was designed to measure about 500 micrometers which was almost the same as the size of one pixel.

In order to reduce the time constant, that is, the product of the junction capacitance and the series resistance, of the diode structure, the diameter of the Schottkey electrode 913 was designed to measure 0.6 micrometers and the distance between the Schottkey electrode 913 and the ohmic electrode 914 was designed to measure 1 micrometer. The Schottkey electrode 913 and the ohmic electrode 914 were Ti electrodes formed by using Ti.

The Ti/Al/TiN wiring 952 (thickness 800 nm) and the Ti/Al/TiN wiring 962 (thickness 800 nm) were placed on a BPSG film 95 (thickness at the thickest place was 2 micrometers) and a TEOS film 96 (thickness 1.6 micrometers), respectively, to form antennas 9621 and 9622. The vias 951 and 961, which had a diameter of 0.4 micrometers and which were filled with CVD-W, connected between the Ti electrodes 913 and 914 and the first wiring 952 and between the first wiring 952 and the second wiring 962, respectively. The detection element 901 was connected to the antennas 9621 and 9622 with series resistance of 4 ohms.

In the present example, the pMOS 902 and the nMOS 903 were produced by the n-well process in the LOCOS method.

As for the pole of each of the source, the drain, and the gate, silicide 924 or silicide 934 were adopted. In the present configuration, the pMOS 902 and the nMOS 903 were formed in such a way that the gate area became relatively large. This is for the purpose of reducing 1/f noises of the CMOS.

Therefore, the gate length and the gate width of the pMOS 902 were designed to measure 0.6 micrometers and 240 micrometers, respectively. The gate length and the gate width of the nMOS 903 were designed to measure 4.8 micrometers and 8 micrometers, respectively. In order to reduce the parasitic capacitance with respect to such a large gate width, the MOS may be divided into, for example, a common centroid layout. They are well known technologies.

The Ti/Al/TiN wiring 952 (thickness 800 nm) and the Ti/Al/TiN wiring 962 (thickness 800 nm) were placed on the BPSG film 95 (thickness at the thickest place was 2 micrometers) and the TEOS film 96 (thickness 1.6 micrometers), respectively. The vias 951 and 961, which had a diameter of 0.4 micrometers, connected between the source, the drain, and the gate of the pMOS 902 and the nMOS 903 and the first wiring 952 and between the first wiring 952 and the second wiring 962, respectively, with relatively low resistance. In this manner, the second circuit 9002 described below was formed.

The circuit 9002 according to the present embodiment was an LNA circuit designed by using a simple source grounded circuit. For example, in the case where a bias of 1 V was applied to the source of the pMOS 902 and the gate of the nMOS 903 and a bias of −1 V was applied to the source of the nMOS 903, the circuit 9002 served as an LNA with the amplification degree of 20 dB and the bandwidth of 10 MHz. The bandwidth was relatively wide and, therefore, for example, noises were able to be reduced by disposing a filter circuit or the like downstream to limit the bandwidth. They are well-known technologies.

In the present example, the circuit 9001 was directly connected to the input stage of the circuit 9002 to effect the zero bias operation of the detection element 901. However, the circuit 9001 may be configured to be brought into non-zero bias operation by using capacitive coupling or the like. As a matter of course, resistance for protection or the like may be inserted into the input stage. Such circuit configurations may be integrated on the same substrate 91 easily.

The imaging element according to the present example was configured to include the circuit 9001 and the circuit 9002 in one pixel, and they were two-dimensionally arrayed. Consequently, a mechanism to read a designated pixel was required. Transistors 904 to access the pixels were transistors, which were connected to the individual pixels, on the same substrate 91, and served as selection switches to read signal voltages and charges of the individual pixels.

The imaging element included a y-address circuit 9004 and y-read line switches 9005. The y-address circuit 9004 operated the y-read line switch 9005 of a read line 9006 to be addressed. Likewise, a y-address circuit 9007 operated a y-read line switch 9008 of a read line 9009 to be addressed. The x-address circuit 9007 and the y-address circuit 9004 may be incorporated with read circuits (not shown in the drawing) of detection signals sent from the individual pixels sequentially.

The imaging element according to the present example was produced as described below. An 8-inch Si substrate 91 was prepared and was subjected to the front end process by using the LOCOS method in the standard CMOS process. Specifically, in the front end process in the present example, the steps shown in FIG. 6A to FIG. 6K and the step shown in FIG. 7L were performed. As a result, an integrated structure of a semiconductor device was formed on the substrate 91.

The Schottkey barrier formation step which was part of the following steps was shown in FIG. 11A to FIG. 11D. Initially, a BPSG film 95 of about 2.5 micrometers was formed as PMD, so as to cover all over the substrate 91 (FIG. 11A). A portion indicated by dotted lines 953 shown in FIG. 11B was removed from the BPSG film 95, and an exposure step to expose part of a region of the substrate 91 surface was performed. As for the method thereof, dry etching was used for the BPSG film and silicide, and wet etching was used for the polysilicon 913 and the gate oxide film 912, as described above.

Thereafter, crystal growth of an epitaxial layer 912 containing SiGe was performed (FIG. 11C). The CVD method was adopted as an epitaxial growth technique and was performed at a relatively low temperature of 550 degrees Celsius. In the low-temperature CVD method, oxygen was contained as an impurity of the raw material gas but the amount was a small 1 by $10^{17}$ cm$^{-3}$ or less. Consequently, a single crystal was able to be grown on only the exposed substrate 91 surface, although a polycrystal remained on the BPSG film 95. However, this polycrystal was able to be removed by CMP thereafter. In some cases, the side surface on the BPSG film 95 side was an amorphous layer or a hollow, although this was able to be removed in island formation thereafter.

Subsequently, a high-concentration ion implant region 9124 was formed. A donor, e.g., phosphorus, was implanted into the region 9124 shown in FIG. 11D, and a heat treatment at, for example, 800 degrees Celsius was performed as activation annealing after the ion implantation. Diffusion of the impurities, e.g., boron, phosphorus, and arsenic, in the pMOS 902 and the nMOS 903 at 800 degrees Celsius was only on the order of several nanometers. This length was one-tenth or less of the gate length and, therefore, it was considered that diffusion did not occur substantially. In the case where residual stress of the BPSG film 95 is present, the high-concentration ion implant region 9124 may be formed after an oxide film, a nitride film, or the like is formed separately in such a way as to cancel the residual stress.

Furthermore, the outermost surface of the epitaxial layer 912 was subjected to hydrofluoric acid cleaning and surface dangling bonds were subjected to modification with hydrogen termination. The electrodes 913 and 914 were formed by using a Ti metal, so that the Schottkey barrier, as shown in FIG. 11D, was formed.

Thereafter, part of the epitaxial layer 912 was removed and islands of the epitaxial layer were formed. The dry etching may be used for formation of the electrode and formation of the islands. The BPSG film 95 of about 3 micrometers was formed, a diode serving as the detection element 901 was embedded and, thereafter, the BPSG film 95 was planarized by CMP. The dotted line 953 indicates the boundary between the thus formed BPSG film in the circuit 9001 region and the BPSG film in the circuit 9002 serving as the amplifier circuit. They may be joined without a seam by using CMP. The Schottkey barrier formation step in the present example was as described above.

Finally, the back end process in the standard CMOS process was performed. As for the order of the steps, making of the vias 951, formation of the first metal wiring 952, formation of the TEOS film 96, making of the vias 961, and formation of the second metal wiring 962 were performed sequentially.

That is, a slender contact hole having a diameter of 0.4 micrometers was made in the BPSG film 95 by a Bosch process or the like and, thereafter, Ti/TiN liner films, 10 nm each, were formed for the purpose of protecting the inner wall of the contact hole. The vias 951 were formed by filling CVD-W at 395 degrees Celsius into the contact hole. Here, CMP was performed again to planarize the BPSG film until the film thickness reached 2 micrometers while W on the BPSG film 95 was removed. A film of Ti/Al/TiN was formed and a wiring pattern was formed by using dry etching, so that the first metal wiring 952 was formed.

Then, the TEOS film 96 was formed having a film thickness somewhat larger than the final thickness of 1.6 micrometers. The vias 961 were made in the same manner as making of the vias 951. Planarization was performed until the film thickness of the TEOS film 96 reached 1.6 micrometers and, thereafter, the second metal wiring 962 was formed by forming a Ti/Al/TiN wiring pattern in the same manner as formation of the above-described first metal wiring 952, so that the imaging element according to the present example was completed.

The thus formed imaging element according to the present example included a semiconductor device which was CMOS-compatible, where the characteristics of the Schottkey barrier were able to be designed.

An image forming apparatus including the imaging element according to the present example and an irradiation device to perform active illumination with millimeter waves or terahertz waves may be constructed. In the frequency region from the millimeter wave band to the terahertz band, background black body radiation energy is small in contrast to the infrared region and, therefore, active illumination is used usually. Examples of irradiation device of electromagnetic waves may include electronic devices including negative resistance elements, e.g., resonant tunneling diodes, Esaki diodes, and Gunn diodes, optical devices, e.g., quantum cascade lasers, p-Ge lasers, and lead-salt lasers, and continuous light sources, e.g., free electron lasers. Alternatively, pulsed light sources, e.g., parametric oscillators, photoconductive elements, Cerenkov radiation LiNbO$_3$ generators, and light-terahertz wave transducers, such as, uni-travelling-carrier (UTC) photodiodes, may be mentioned.

A subject is irradiated with an irradiation device. Terahertz waves passed through the subject or reflected at the subject include the information of the subject, and the resulting terahertz waves are acquired by an imaging element. At that time, in the case where an objective lens is disposed between the imaging element and the specimen, a focal plane array type is constructed and, thereby, the image forming apparatus may pick up an image in one shot.

Also, a contact type image forming apparatus is considered as another example. In the configuration of this case, the secondary information of the specimen may be obtained by contact of the specimen with the imaging element. In this case, an objective lens is unnecessary.

In addition, it is expected that the semiconductor device according to the present invention is applied to a sensor usable for production control, medical diagnostic imaging, safety control, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-267156, filed Dec. 25, 2013 and No. 2014-245236, filed Dec. 3, 2014, which are hereby incorporated by reference herein in their entirety.

The invention claimed is:

1. A semiconductor device comprising:
a silicon substrate; and
a Schottkey barrier element, a p-type MOS transistor, and an n-type MOS transistor which are arranged in an in-plane direction on the silicon substrate,
wherein the Schottkey barrier element includes a semiconductor layer and electrodes, and the semiconductor layer and the electrodes are in contact with each other to form the Schottkey barrier element,
the semiconductor layer is arranged
(i) just above a layer having the same chemical composition as those of an impurity diffusion layer in the source or drain of the p-type MOS transistor,
(ii) just above a layer having the same chemical composition as those of an impurity diffusion layer in the source or drain of the n-type MOS transistor,
(iii) just above a region, in the silicon substrate, having the same chemical composition as those of a channel region, in the silicon substrate, just below a gate oxide film of the p-type MOS transistor or the n-type MOS transistor, or
(iv) just above a region, in the silicon substrate, having the same chemical composition as those of a region, in the silicon substrate, just below a field oxide film disposed between the p-type MOS transistor and the n-type MOS transistor.

2. The semiconductor device according to claim 1, wherein the semiconductor layer is an epitaxial layer.

3. The semiconductor device according to claim 1, wherein the field oxide film is arranged between the Schottkey barrier element and the p-type MOS transistor or the n-type MOS transistor.

4. The semiconductor device according to claim 1, wherein the height of the Schottkey barrier is 0.4 eV or less.

5. The semiconductor device according to claim 1, wherein the height of the Schottkey barrier is 0.1 eV or more and 0.3 eV or less.

6. The semiconductor device according to claim 1, wherein the semiconductor layer has a lattice constant of 5.430 angstroms or more and 5.653 angstroms or less.

7. The semiconductor device according to claim 1, wherein the Schottkey barrier element includes a Schottkey barrier diode or MOSFET.

8. The semiconductor device according to claim 1, wherein the semiconductor layer includes a semiconductor having a conductivity type opposite to the conductivity type of the impurity diffusion layer.

9. The semiconductor device according to claim 1, wherein the semiconductor layer includes a semiconductor having a conductivity type opposite to the conductivity type of the silicon substrate.

10. An image forming apparatus to form an image of a specimen, comprising:
an irradiation device to perform illumination of electromagnetic waves to the specimen; and
an imaging element to detect electromagnetic waves from the specimen,
wherein the imaging element includes the semiconductor device according to claim 1.

11. The semiconductor device according to claim 1, wherein the semiconductor layer is arranged
(i) just above a layer having the same chemical composition and height as those of an impurity diffusion layer in the source or drain of the p-type MOS transistor,
(ii) just above a layer having the same chemical composition and height as those of an impurity diffusion layer in the source or drain of the n-type MOS transistor,
(iii) just above a region, in the silicon substrate, having the same chemical composition and height as those of a channel region, in the silicon substrate, just below a gate oxide film of the p-type MOS transistor or the n-type MOS transistor, or
(iv) just above a region, in the silicon substrate, having the same chemical composition and height as those of a region, in the silicon substrate, just below a field oxide film disposed between the p-type MOS transistor and the n-type MOS transistor.

12. A method for manufacturing a semiconductor device including a Schottkey barrier element, a p-type MOS transistor, and an n-type MOS transistor on a silicon substrate, the method comprising the steps of:
a first process of forming the n-type MOS transistor, the p-type MOS transistor, and the Schottky barrier element, on the silicon substrate;
a second process of connecting metal wiring to each of the n-type MOS transistor, the p-type MOS transistor, and the Schottky barrier element formed in the first process,
wherein, in the first process, an element formation process of forming the Schottky barrier element is performed, after performing a process including at least a first step of forming a gate oxide film on the silicon substrate, a second step of forming a field oxide film on the silicon substrate to separate elements, and a third step of forming an impurity diffusion layer, and
wherein the element formation process includes
an exposing step to expose the impurity diffusion layer formed in the third step, a region just below the gate oxide film formed in the first step, or a region just below the field oxide film formed in the second step,
a growing step to epitaxially grow a semiconductor layer just above the impurity diffusion layer, the region just below the gate oxide film, or the region just below the field oxide film, which is exposed in the exposing step, and
an electrode forming step to form an electrodes on the surface of the semiconductor layer to form the semiconductor layer and the Schottky barrier element.

13. The manufacturing method according to claim 12, wherein the impurity diffusion layer provided with the semiconductor layer is formed at the same time with the impurity diffusion layer in the source or drain of the p-type MOS transistor or the impurity diffusion layer in the source or drain of the n-type MOS transistor.

14. The manufacturing method according to claim 12, wherein the region, which is provided with the semiconductor layer and which is just below the gate oxide film, is formed in the same step as the step of a channel region, in the substrate, just below the gate oxide film of the p-type MOS transistor or the n-type MOS transistor.

15. The manufacturing method according to claim 12, wherein the region, which is provided with the semiconductor layer and which is just below the field oxide film, is a region, from which an oxide film formed at the same time with the field oxide film formed between the p-type MOS transistor and the n-type MOS transistor has been removed.

16. The manufacturing method according to claim 12, wherein in the growing step, the semiconductor layer is epitaxially grown by using a chemical vapor deposition method, a metal-organic vapor phase epitaxy method, or a molecular beam epitaxy method.

\* \* \* \* \*